US010689580B2

(12) United States Patent
Kobilka et al.

(10) Patent No.: US 10,689,580 B2
(45) Date of Patent: *Jun. 23, 2020

(54) FLAME-RETARDANT VANILLIN-DERIVED MONOMERS

(71) Applicant: International Business Machines Corporation, Armonk, NY (US)

(72) Inventors: Brandon M. Kobilka, Tuscon, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/371,689

(22) Filed: Apr. 1, 2019

(65) Prior Publication Data

US 2019/0225888 A1 Jul. 25, 2019

Related U.S. Application Data

(62) Division of application No. 15/584,838, filed on May 2, 2017, now Pat. No. 10,266,772.

(51) Int. Cl.
| | |
|---|---|
| *C09K 21/12* | (2006.01) |
| *C08K 5/5337* | (2006.01) |
| *C08K 5/5313* | (2006.01) |
| *C08K 5/5317* | (2006.01) |
| *C07D 317/12* | (2006.01) |
| *C09K 21/14* | (2006.01) |
| *C07F 9/655* | (2006.01) |
| *C07F 9/12* | (2006.01) |
| *C07F 9/14* | (2006.01) |
| *C07F 9/40* | (2006.01) |
| *C07C 15/04* | (2006.01) |

(52) U.S. Cl.
CPC .............. *C09K 21/12* (2013.01); *C07C 15/04* (2013.01); *C07D 317/12* (2013.01); *C07F 9/12* (2013.01); *C07F 9/1406* (2013.01); *C07F 9/4021* (2013.01); *C07F 9/65502* (2013.01); *C07F 9/65515* (2013.01); *C08K 5/5313* (2013.01); *C08K 5/5317* (2013.01); *C08K 5/5337* (2013.01); *C09K 21/14* (2013.01)

(58) Field of Classification Search
CPC ..... C09K 21/12; C09K 21/14; C07F 9/65502; C07F 9/4021; C07F 9/1406; C07F 9/12; C07F 9/65515; C08K 5/5317; C08K 5/5313; C08K 5/5337; C07D 317/12
USPC ........................................................ 524/27
See application file for complete search history.

(56) References Cited

U.S. PATENT DOCUMENTS 4,255,319 A * 3/1981 Peters ..................... C08K 3/02
                                                              106/18.18

FOREIGN PATENT DOCUMENTS

| CN | 107011499 A | 8/2017 |
| JP | 2013185039 A | 9/2013 |
| WO | 2016172353 A1 | 10/2016 |
| WO | 2017007883 A1 | 1/2017 |

OTHER PUBLICATIONS

Wang et al., Macromolecules, 50, 1892-1901, 2017. (Year: 2017).*
Fache et al., "Epoxy thermosets from model mixtures of the lignin-to-vanillin process," Green Chemistry, 2016, 18, pp. 712-725, The Royal Society of Chemistry. DOI: 10.1039/c5gc01070e.
Fache et al., "Vanillin, a key-intermediate of biobased polymers," European Polymer Journal, 2015, vol. 68, pp. 488-502, Elsevier. DOI: 10.1016/j.eurpolymj.2015.03.050.
Fache et al., "Vanillin, a promising biobased building-block for monomer synthesis," Green Chemistry, 2014, 16, pp. 1987-1998, The Royal Society of Chemistry. DOI: 10.1039/c3gc42613k.
Illy et al., "Phosphorylation of bio-based compounds: the state of the art," Polymer Chemistry, 2015, 6 (35), pp. 3257-6291, The Royal Society of Chemistry DOI: 10.1039/c5py00812c.
Smolarski, N., "High-Value Opportunities for Lignin: Unlocking its Potential," Frost & Sullivan, Market Insight, Nov. 7, 2012, pp. 1-15.
Stanzione, III, J., "S15.2. Vanillin: A Renewable and Versatile Platform Chemical for Sustainable Polymers," 14th International Symposium on Bioplastics, Biocomposites, and Biorefining, (May 31-Jun. 3, 2016), Jun. 22, 2016, pp. 1-26.
Kobilka et al., "Bondable Flame-Retardant Vanillin-Derived Molecules," U.S. Appl. No. 15/584,753, filed May 2, 2017.
Kobilka et al., "Flame-Retardant Vanillin-Derived Cross-Linkers," U.S. Appl. No. 15/584,798, filed May 2, 2017.
Kobilka et al., "Flame-Retardant Vanillin-Derived Monomers," U.S. Appl. No. 15/584,838, filed May 2, 2017.
Kobilka et al., "Flame-Retardant Vanillin-Derived Small Molecules," U.S. Appl. No. 15/584,866 filed May 2, 2017.

(Continued)

*Primary Examiner* — Hui H Chin
(74) *Attorney, Agent, or Firm* — Kelsey M. Skodje

(57) ABSTRACT

A flame-retardant vanillin-derived monomer, a process for forming a flame-retardant polymer, and an article of manufacture comprising a material that contains flame-retardant vanillin-derived monomer are disclosed. The flame-retardant vanillin-derived monomer can be synthesized from vanillin obtained from a bio-based source, and can have at least one phosphoryl or phosphonyl moiety with phenyl, allyl, epoxide, or propylene carbonate substituents. The process for forming the flame-retardant polymer can include reacting a vanillin derivative and a flame-retardant phosphorus-based molecule to form the flame-retardant vanillin-derived monomer, and then polymerizing the flame-retardant vanillin-derived monomer. The material in the article of manufacture can be flame-retardant, and contain the flame-retardant vanillin-derived monomer. Examples of materials that can be in the article of manufacture can include resins, plastics, adhesives, polymers, etc.

9 Claims, 22 Drawing Sheets

(56) References Cited

OTHER PUBLICATIONS

Kobilka et al., "Bondable Flame-Retardant Vanillin-Derived Molecules," U.S. Appl. No. 15/850,681, filed Dec. 21, 2017.
Kobilka et al., "Flame-Retardant Vanillin-Derived Cross-Linkers," U.S. Appl. No. 15/850,738, filed Dec. 21, 2017.
Kobilka et al., "Flame-Retardant Vanillin-Derived Monomers," U.S. Appl. No. 15/850,784, filed Dec. 21, 2017.
Kobilka et al., "Flame-Retardant Vanillin-Derived Small Molecules," U.S. Appl. No. 15/850,838, filed Dec. 21, 2017.
Kobilka et al., "Bondable Flame-Retardant Vanillin-Derived Molecules," U.S. Appl. No. 16/212.954, filed Dec. 7, 2018.
Kobilka et al., "Flame-Retardant Vanillin-Derived Cross-Linkers," U.S. Appl. No. 16/237695, filed Jan. 1, 2019.
Kobilka et al., "Flame-Retardant Vanillin-Derived Small Molecules," U.S. Appl. No. 16/276,878, filed Feb. 15, 2019.
List of IBM Patents or Patent Applications Treated as Related, Signed Apr. 1, 2019, 2 pages.

\* cited by examiner

FLAME-RETARDANT VANILLIN-DERIVED MONOMERS

BACKGROUND

The present disclosure relates to bio-renewable flame-retardant compounds and, more specifically, flame-retardant vanillin-derived monomers.

Bio-based compounds provide a source of renewable materials for various industrial applications, such as polymers, flame retardants, cross-linkers, etc. One example of a bio-based compound that can be used in these applications is vanillin (4-hydroxy-3-methoxybenzaldehyde). Vanillin is a plant metabolite and the main component of natural vanilla extract. While vanillin can be obtained from vanilla extract, or synthesized from petroleum-based raw materials, a number of biotechnology processes are also used to produce vanillin. These processes can be plant-based or microorganism-based, and provide a renewable source of vanillin on an industrial scale.

SUMMARY

Various embodiments are directed to flame-retardant vanillin-derived monomers. The flame-retardant vanillin-derived monomers can have at least one phosphoryl or phosphonyl moiety. Each phosphoryl or phosphonyl moiety can have at least one substituent selected from a group consisting of a phenyl substituent, an allyl substituent, an epoxide substituent, and a propylene carbonate substituent. The flame-retardant vanillin-derived monomers can be synthesized from vanillin obtained from a bio-based source. Additional embodiments are directed to forming a flame-retardant polymer. The polymer can be produced by forming a vanillin derivative, forming a phosphorus-based flame-retardant molecule, and reacting the vanillin derivative and the phosphorus-based flame-retardant molecule with one another to form a flame-retardant vanillin-derived monomer. The flame-retardant vanillin-derived monomer can then be polymerized, forming the flame-retardant polymer. The vanillin derivative can be a flame-retardant phenol vanillin derivative, a flame-retardant carboxylic acid vanillin derivative, a flame-retardant benzyl alcohol vanillin derivative, a phenol diol vanillin derivative, a carboxylic acid diol derivative, a benzyl alcohol diol vanillin derivative. The phosphorus-based flame-retardant molecule can be a phosphate-based molecule or a phosphonate-based molecule with at least one phenyl substituent, allyl substituent, epoxide substituent, or propylene carbonate substituent. Further embodiments are directed to an article of manufacture comprising a material that contains the flame-retardant vanillin-derived monomer. The material can be a resin, plastic, adhesive, polymer, etc. The article of manufacture can also comprise a printed circuit board.

DETAILED DESCRIPTION

Bio-based compounds are increasingly being used in the synthesis of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies can include plant-based or microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of substances that can be produced from bio-based compounds can include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can also impart flame-retardant properties to bio- and petroleum-based polymers. For example, flame-retardant monomers or cross-linkers can be incorporated into polymers. Additionally, flame-retardant molecules can be blended or chemically reacted with the polymers.

Vanillin (4-hydroxy-3-methoxybenzaldehyde) is one example of a bio-based compound that has applications as a component of various polymers, resins, and small molecules. Vanillin is a plant metabolite and the main component of natural vanilla extract. It can be obtained from the plant- and microorganism-based bio-sources discussed above, or synthesized from petroleum-based raw materials. According to some embodiments of the present disclosure, vanillin is used as a precursor for flame-retardant monomers. These vanillin-derived flame-retardant monomers polymerize to form flame-retardant polymers.

Figure 1:
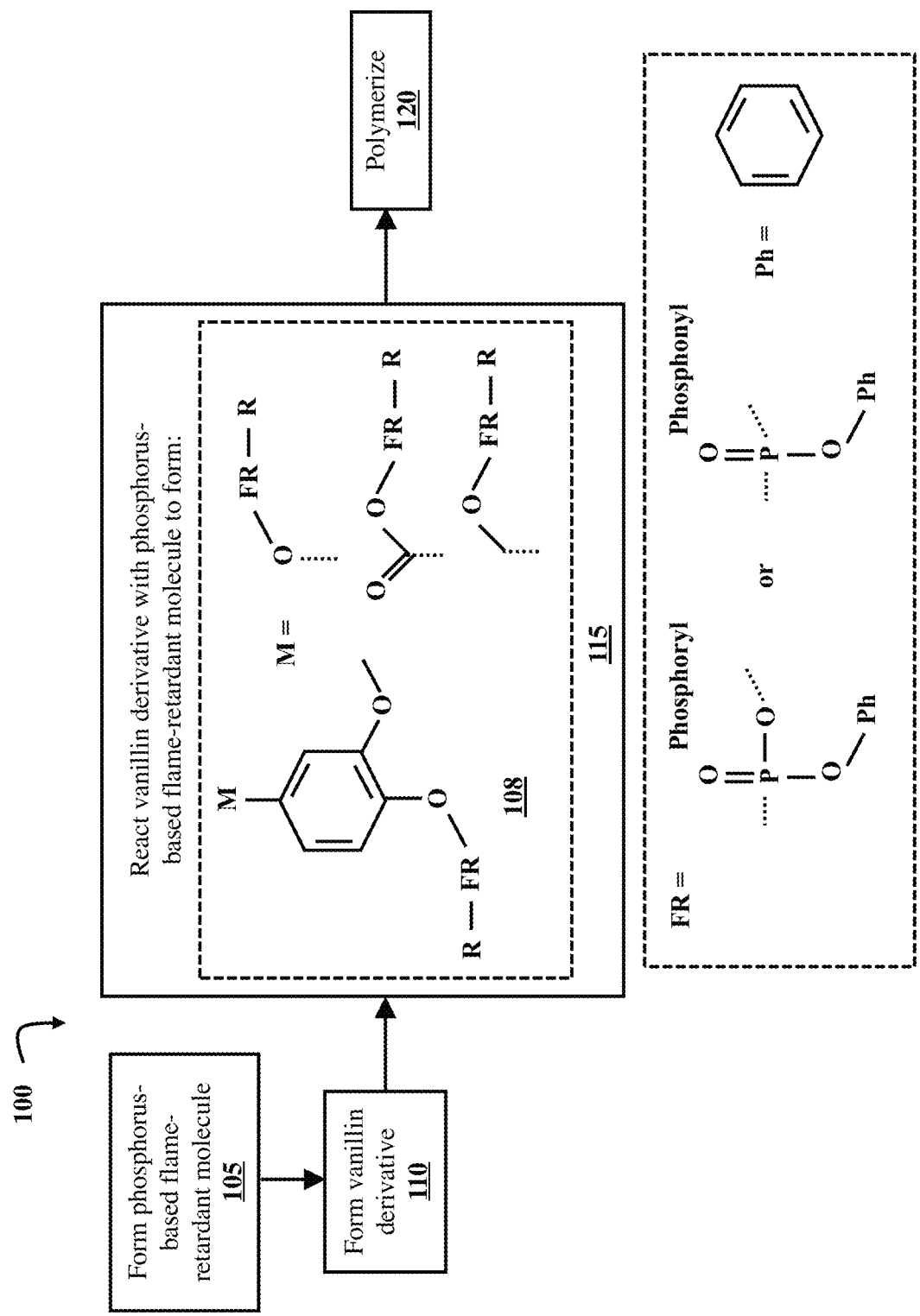
FIG. 1 is a flow diagram illustrating a process of forming a flame-retardant polymer from flame-retardant vanillin-derived monomers, according to embodiments of the present disclosure.

FIG. 1 is a flow diagram 100 illustrating a process of forming a flame-retardant polymer from flame-retardant vanillin-derived monomers 108, according to embodiments of the present disclosure. The vanillin-derived monomers 108 can be bis-functionalized or mono-functionalized. The mono-functionalized flame-retardant vanillin-derived monomers have one functional group that participates in the polymerization, while the bis-functionalized monomers have two functional groups that participate in the polymerization. Process 100 begins with the formation of a phosphorus-based flame-retardant molecule. This is illustrated at step 105. The phosphorus-based flame-retardant molecule has either a phosphoryl or phosphonyl moiety (collectively referred to as an FR group) with an attached R group. Examples of R groups that can be attached to the FR group can include phenyl substituents, epoxide substituents, allyl substituents, and propylene carbonate substituents. The phenyl substituents do not participate in the polymerization reactions. The syntheses and structures of phosphorus-based flame-retardant molecules are discussed in greater detail with regard to FIGS. 3, and 4A-4D.

Process 100 continues with the formation of a vanillin derivative. This is illustrated at step 110. The vanillin derivative is either a diol vanillin derivative with two hydroxyl groups or a flame-retardant vanillin derivative that has one flame-retardant group and one hydroxyl group. The diol vanillin derivatives are formed in a reaction that replaces vanillin's aldehyde group with a hydroxyl. The flame-retardant vanillin derivatives are formed by a reaction of vanillin with the phosphorus-based flame-retardant molecule and a reaction that replaces vanillin's aldehyde functional group with a hydroxyl group. Examples of reactions that can convert the aldehyde group to a hydroxyl group can include oxidation by sodium percarbonate, oxidation by potassium permanganate, and reduction by sodium borohydride.

Figure 2A:
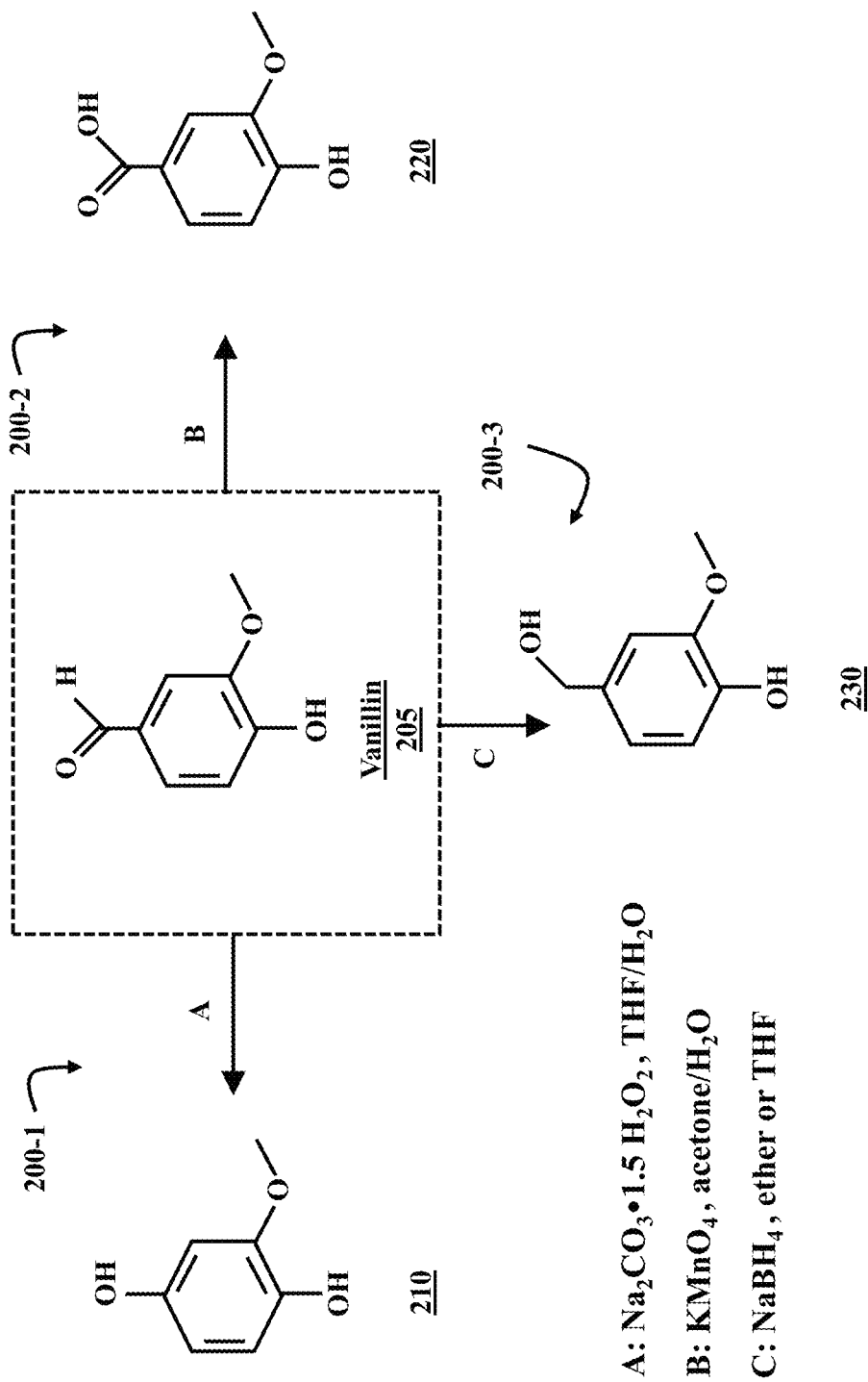
FIG. 2A is a chemical reaction diagram illustrating processes of synthesizing three diol vanillin derivatives, according to embodiments of the present disclosure.
Figure 2B:
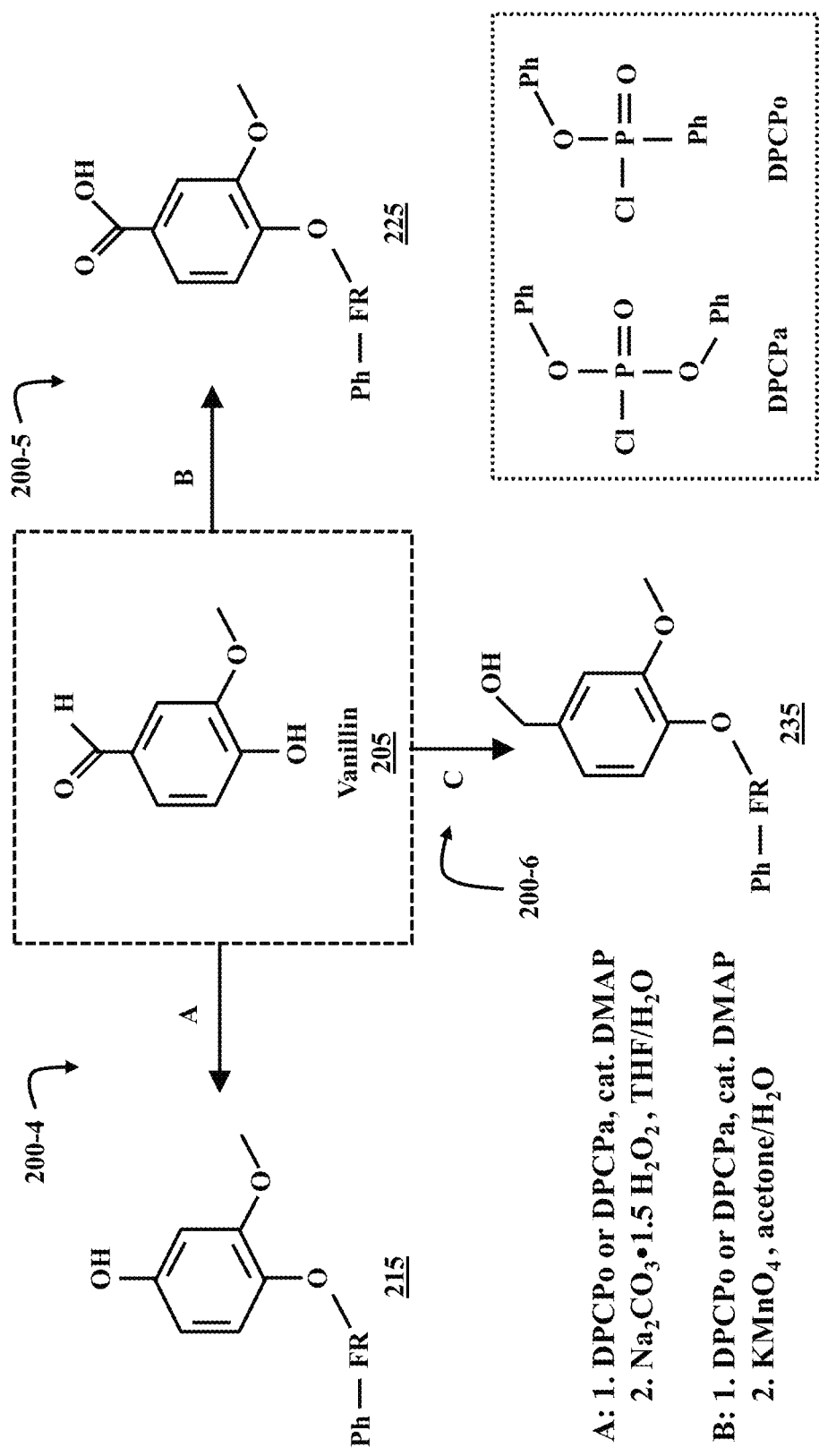
FIG. 2B is a chemical reaction diagram illustrating processes of synthesizing three flame-retardant vanillin derivatives, according to embodiments of the present disclosure.

The structures and syntheses of the diol vanillin derivatives are discussed in greater detail with regard to FIG. 2A, and the structures and syntheses of the flame-retardant vanillin derivatives are discussed in greater detail with regard to FIG. 2B. It should be noted that the formation of the vanillin derivative at step 110 is illustrated as occurring after the formation of the phosphorus-based flame-retardant molecule at step 105. However, in some embodiments, step 110 can occur before step 105.

The vanillin derivative and the phosphorus-based flame-retardant molecule are chemically reacted in order to form a flame-retardant vanillin-derived monomer 108. This is illustrated at step 115. The identity of the M group on the flame-retardant vanillin-derived monomer 108 is determined by the phosphorus-based flame-retardant molecule and the vanillin derivative used in the reaction. The phosphorus-based flame-retardant molecules react with hydroxyl groups on the vanillin derivatives synthesized in step 105 to provide the FR group with the attached R group. Examples of FR groups, as well as the syntheses and structures of flame-retardant vanillin-derived monomers 108 are discussed in greater detail with regard to FIGS. 5A-5L.

The flame-retardant vanillin-derived monomer 108 is polymerized under a variety of reaction conditions. This is illustrated at step 120. The reaction conditions under which the polymerization occurs are discussed in greater detail with regard to FIGS. 6A-6D. The polymerization of the flame-retardant vanillin-derived monomers 108 forms a variety of flame-retardant polymers that have a number of applications, as is discussed in greater detail below.

FIG. 2A is a chemical reaction diagram illustrating processes 200-1, 200-2, and 200-3 of synthesizing three diol vanillin derivatives, according to embodiments of the present disclosure. The three diol vanillin derivatives are a phenol diol derivative 210, a carboxylic acid diol derivative 220, and a benzyl alcohol diol derivative 230. These vanillin derivatives are precursors for the bis-functionalized flame-retardant vanillin-derived monomers 108. The syntheses of the bis-functionalized flame-retardant vanillin-derived monomers 108 from the diol vanillin derivatives are described in greater detail with regard to FIGS. 5A, 5B, 5E, 5F, 5I, and 5J.

In process 200-1, the phenol diol derivative 210 of vanillin is produced in an oxidation reaction with sodium percarbonate. Deionized water is added to a solution of vanillin 205 in tetrahydrofuran (THF). The resulting vanillin/THF/$H_2O$ solution is degassed with an inert gas (e.g., argon or nitrogen). While agitating the mixture, sodium percarbonate ($Na_2CO_3.1.5H_2O_2$) is added until pH=3 is reached, thus quenching the reaction. After quenching the reaction, the THF is evaporated, and the aqueous phase is extracted with ethyl acetate. The organic phases are collected, washed with brine, and dried over anhydrous sodium sulfate ($Na_2SO_4$). The ethyl acetate is removed under reduced pressure, yielding the isolated phenol diol derivative 210.

In process 200-2, the carboxylic acid diol derivative 220 of vanillin is produced in an oxidation reaction with potassium permanganate. Potassium permanganate ($KMnO_4$) is added to an acetone/$H_2O$ solution of vanillin 205. The mixture is stirred for approximately 1.5 hours at room temperature. Sodium bisulfite ($NaHSO_3$) in hydrochloric acid (HCl) is added to the resulting purple mixture until the mixture is colorless. The mixture is extracted with ethyl acetate, and the organic phases are collected, washed with brine, and dried over anhydrous magnesium sulfate ($MgSO_4$). The ethyl acetate is removed under reduced pressure, yielding the isolated carboxylic acid diol derivative 220.

In process 200-3, the benzyl alcohol diol derivative 230 of vanillin is produced in a reduction reaction with sodium borohydride. Sodium borohydride ($NaBH_4$) is added to a solution of vanillin 205 in anhydrous ether or tetrahydrofuran (THF). The mixture is stirred at room temperature under an inert gas (e.g., argon or nitrogen) for approximately four hours. The mixture is then concentrated, and purified by column chromatography to give the benzyl alcohol diol derivative 230 as a colorless oil.

FIG. 2B is a chemical reaction diagram illustrating processes 200-4, 200-5, and 200-6 of synthesizing three flame-retardant vanillin derivatives, according to embodiments of the present disclosure. The three flame-retardant vanillin derivatives are a phenol flame-retardant derivative 215, a carboxylic acid flame-retardant derivative 225, and a benzyl alcohol flame-retardant derivative 235. These vanillin derivatives are precursors for the mono-functionalized flame-retardant vanillin-derived monomers 108. The syntheses of the mono-functionalized flame-retardant vanillin-derived monomers 108 are described in greater detail with regard to FIGS. 5C, 5D, 5G, 5H, 5K, and 5L.

In process 200-4, the phenol flame-retardant derivative 215 of vanillin is produced. The first step in this reaction replaces vanillin's hydroxyl group with an FR group. The FR group is provided by a reaction between vanillin 205 and either diphenyl chlorophosphate (DPCPa) or diphenylphosphinic chloride (DPCPo), as well as catalytic dimethylaminopyridine (DMAP). In some embodiments, stoichiometric triethylamine is used instead of DMAP. If the reaction is carried out with DPCPa, the phenol flame-retardant derivative 215 will have phosphoryl FR groups, and, if the reaction is carried out with DPCPo, the phenol flame-retardant derivative 215 will have phosphonyl FR groups.

In the second step in process 200-4, deionized water ($H_2O$) and tetrahydrofuran (THF) are added to the reaction. The resulting mixture is degassed with an inert gas (e.g., argon or nitrogen). While agitating the mixture, sodium percarbonate ($Na_2CO_3.1.5H_2O_2$) is added until pH=3 is reached, thus quenching the reaction. After quenching the reaction, the THF is evaporated, and the aqueous phase is extracted with ethyl acetate. The organic phases are collected, washed with brine, and dried over anhydrous sodium sulfate ($Na_2SO_4$). The ethyl acetate is removed under reduced pressure, yielding the isolated phenol derivative 215.

In process 200-5, the carboxylic acid flame-retardant derivative 225 of vanillin is produced. The first step in this reaction replaces vanillin's hydroxyl group with an FR group, and is carried out under substantially the same conditions as the first step in process 200-4. In the second step, potassium permanganate ($KMnO_4$) in an acetone/$H_2O$ solution is added to the reaction. The mixture is stirred for approximately 1.5 hours at room temperature. A solution of sodium bisulfite ($NaHSO_3$) in hydrochloric acid (HCl) is added to the resulting purple mixture until the mixture is colorless. The mixture is extracted with ethyl acetate, and the organic phases are collected, washed with brine, and dried over anhydrous magnesium sulfate ($MgSO_4$). The ethyl acetate is removed under reduced pressure, yielding the isolated carboxylic acid flame-retardant derivative 225.

In process 200-6, the benzyl alcohol flame-retardant derivative 235 is produced. The first step in this reaction replaces vanillin's hydroxyl group with an FR group, and is carried out under substantially the same conditions as the first step in process 200-4. In the second step, sodium borohydride ($NaBH_4$) is added to a solution of vanillin 205 in anhydrous ether or tetrahydrofuran (THF). The mixture is stirred at room temperature under an inert gas (e.g., argon or nitrogen) for approximately four hours. The mixture is then concentrated, and purified by column chromatography to give the benzyl alcohol flame-retardant derivative 235.

Figure 3:
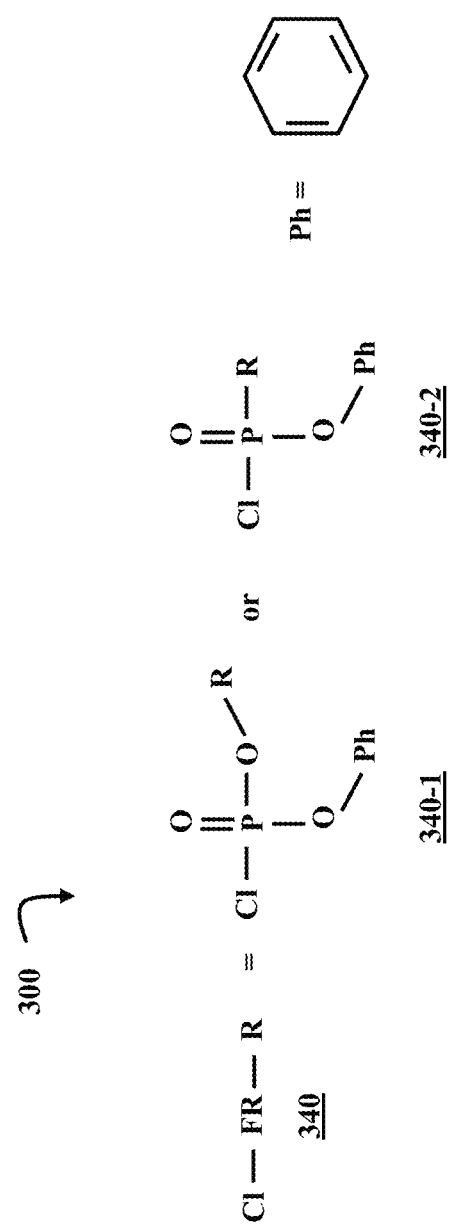
FIG. 3 is a diagrammatic representation of the molecular structures of generic phosphorus-based flame-retardant molecules, according to embodiments of the present disclosure.

FIG. 3 is a diagrammatic representation of the molecular structures 300 of generic phosphorus-based flame-retardant molecules 340, according to embodiments of the present disclosure. Each phosphorus-based flame-retardant molecule 340 is either a phosphate-based flame-retardant molecule 340-1 or a phosphonate-based flame-retardant molecule 340-2. Herein, phosphoryl and phosphonyl moieties are replaced by the abbreviation "FR" in order to simplify illustrations of the molecular structures. Each phosphorus-based flame-retardant molecule 340 has a phenyl (Ph) substituent and an R group.

The identities of the R groups bound to the flame-retardant molecules 340 vary, and are discussed in greater detail with respect to FIGS. 4A, 4B, 5B, 5D, 5F, 5H, 5J, and 5L. Additionally, in some embodiments, the phenyl group is replaced by another alkyl substituent (e.g., methyl, ethyl, propyl, isopropyl, etc.). The syntheses of the phosphorus-based flame-retardant molecules 340 are discussed with regard to FIGS. 4A and 4B. The phosphorus-based flame-retardant molecules 340 are reacted with the vanillin derivatives 210, 215, 220, 225, 230, and 235 to form flame-retardant vanillin-derived monomers 108. These reactions are discussed in greater detail with regard to FIGS. 5A, 5C, 5E, 5G, 5I, and 5K.

Figure 4A:
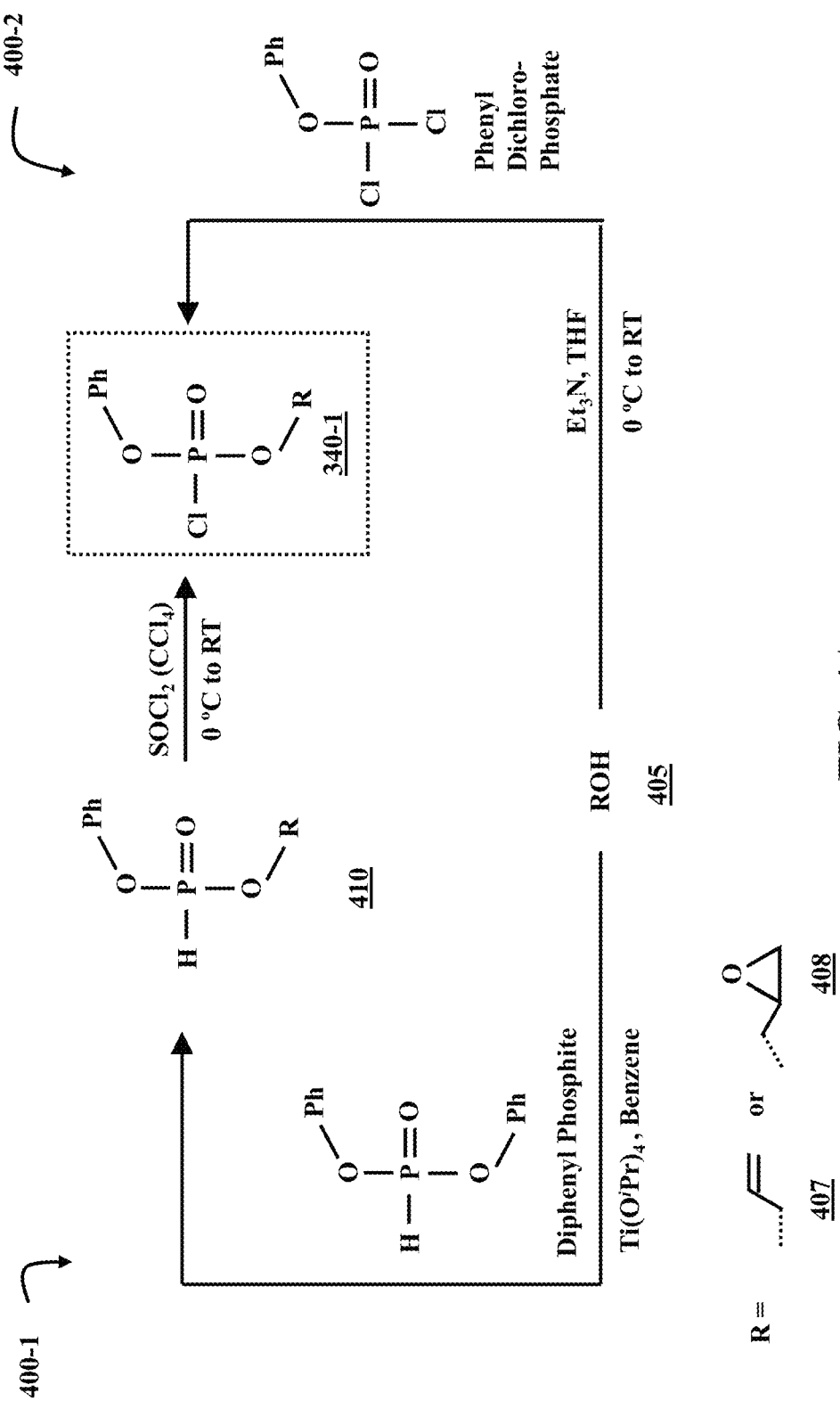
FIG. 4A is a chemical reaction diagram illustrating two processes of synthesizing the phosphate-based flame-retardant molecule, according to embodiments of the present disclosure.

FIG. 4A is a chemical reaction diagram illustrating two processes 400-1 and 400-2 of synthesizing the phosphate-based flame-retardant molecule 340-1, according to embodiments of the present disclosure. In both processes 400-1 and 400-2, an alcohol 405 is a starting material for the phosphate-based flame-retardant molecule 340-1. The alcohol 405 has either an allyl R group 407 or an epoxide R group 408. It should be noted that, though an allyl group 407 with a single methylene spacer group is illustrated here, other alcohols with allylic chains of varying lengths (e.g., one to twelve methylene spacer groups) could be used. Additionally, alcohols with acrylate substituents are used in some embodiments.

In process 400-1, the alcohol 405 is reacted with diphenyl phosphite and titanium isopropoxide (Ti(O$^i$Pr)$_4$) in benzene to produce a precursor 410 to the phosphate-based flame-retardant molecule 340-1. In this pseudo-transesterification reaction, the precursor 410 is formed when a phenyl (Ph) substituent on diphenyl phosphite is replaced by an allyl 407 or epoxide 408 R group from the alcohol 405. The precursor 410 is then reacted with thionyl chloride (SOCl$_2$) and carbon tetrachloride (CCl$_4$) over a range of 0° C. to room temperature (RT), forming the phosphate-based flame-retardant molecule 340-1 with an allyl 407 or epoxide 408 R group.

In process 400-2, the alcohol 405 is reacted with phenyl dichlorophosphate in a tetrahydrofuran (THF) solution containing triethyl amine (Et$_3$N). This process is carried out over a range of 0° C. to room temperature (RT). A chloride on the phenyl dichlorophosphate is replaced by the allyl 407 or epoxide 408 R group from the alcohol 405, forming the phosphate-based flame-retardant molecule 340-1 with an allyl 407 or epoxide 408 R group.

Figure 4B:
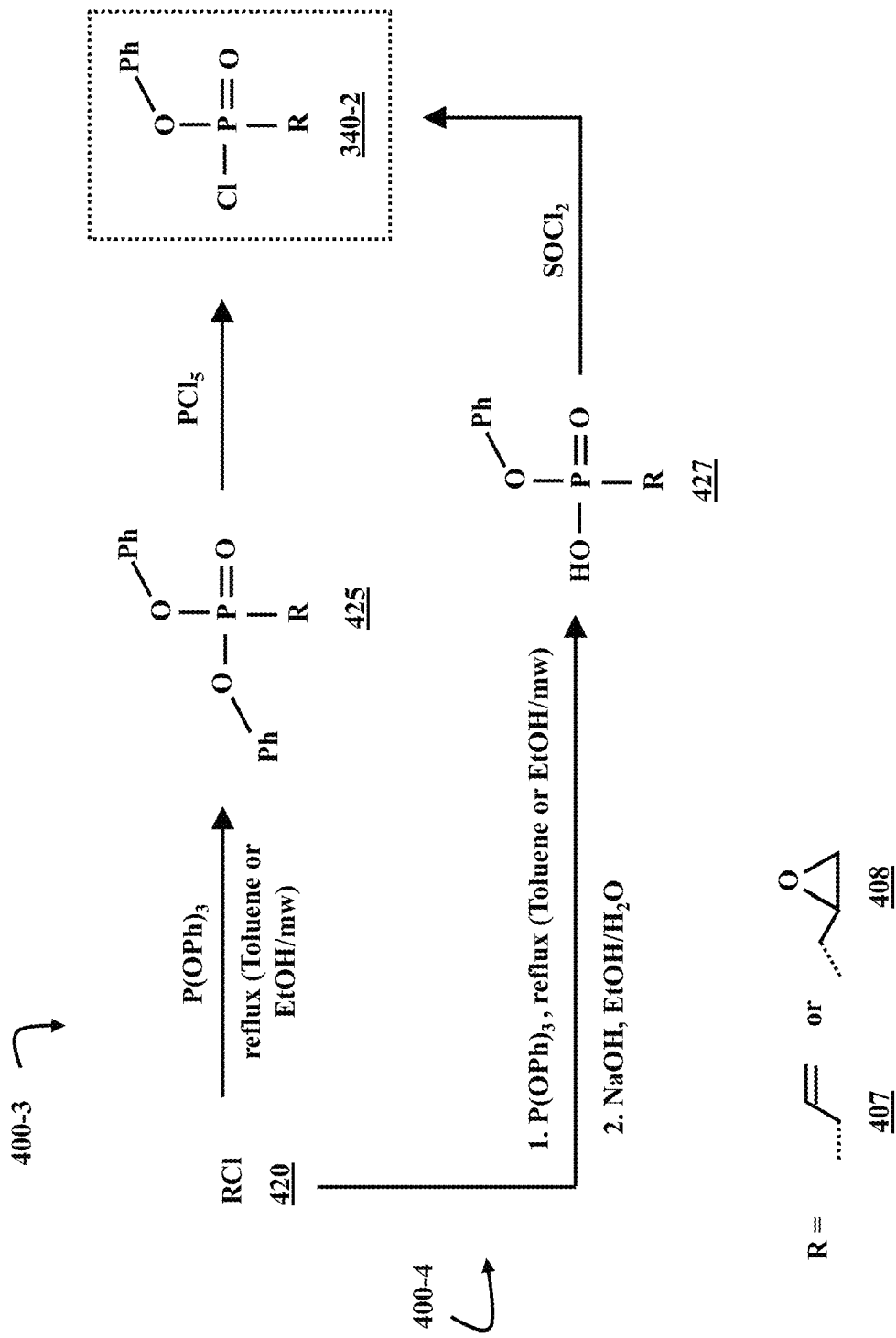
FIG. 4B is a chemical reaction diagram illustrating two processes of synthesizing the phosphonate-based flame-retardant molecule, according to embodiments of the present disclosure.

FIG. 4B is a chemical reaction diagram illustrating two processes 400-3 and 400-4 of synthesizing the phosphonate-based flame-retardant molecule 340-2, according to embodiments of the present disclosure. In both processes 400-3 and 400-4, an organochloride 420 is a starting material for the phosphonate-based flame-retardant molecule 340-2. The organochloride has either an allyl R group 407 or an epoxide R group 408. It should be noted that, as in the case of the alcohol 405, other organochlorides with allylic chains of varying lengths (e.g., one to twelve methylene spacer groups) could be used. Additionally, organochlorides with acrylate substituents are used in some embodiments.

In process 400-3, the organochloride 420 is reacted with triphenyl phosphite (P(OPh)$_3$). The mixture is heated, either by refluxing in toluene or microwaving (mw) in ethanol (EtOH), producing a phosphonyl ester precursor 425 to the phosphonate-based flame-retardant molecule 340-2. The phosphonyl ester precursor 425 is reacted with phosphorus pentachloride (PCl$_5$) to form the phosphonate-based flame-retardant molecule 340-2 with an allyl 307 or epoxide 308 R group.

In process 400-4, a mixture of organochloride 420 and triphenyl phosphite (P(OPh)$_3$) is heated, either by refluxing in toluene or microwaving (mw) in ethanol (EtOH), forming a phenylphosphinic acid precursor 427 to the phosphonate-based flame-retardant molecule 340-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 427, producing the phosphonate-based flame-retardant molecule 340-2 with an allyl 307 or epoxide 308 R group.

Figure 5A:
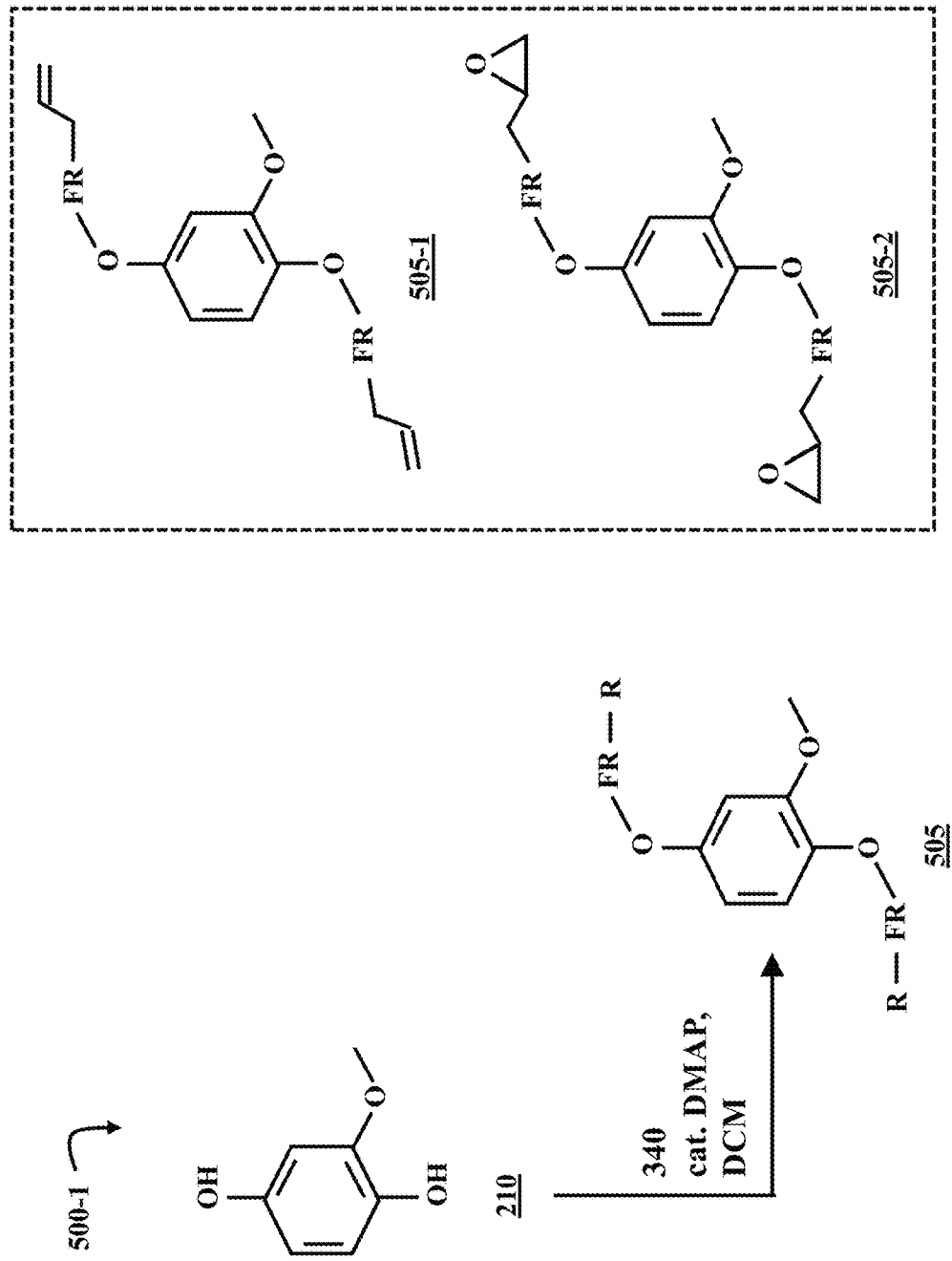
FIG. 5A is a chemical reaction diagram illustrating a process of synthesizing a bis-functionalized flame-retardant phenol vanillin-derived monomer, according to some embodiments of the present disclosure.

FIG. 5A is a chemical reaction diagram illustrating a process 500-1 of synthesizing a bis-functionalized flame-retardant phenol vanillin-derived monomer 505, according to some embodiments of the present disclosure. In process 500-1, the phenol diol derivative 210 of vanillin is reacted with a phosphorus-based flame-retardant molecule 340 and catalytic dimethylaminopyridine (DMAP) in a dichloromethane (DCM) solution. In some embodiments, stoichiometric triethylamine is used instead of DMAP. Stirring this mixture yields the bis-functionalized flame-retardant phenol vanillin-derived monomer 505.

If process 500-1 is carried out with a phosphorus-based flame-retardant molecule 340 having an allyl R group 407, the bis-functionalized flame-retardant phenol vanillin-derived monomer 505 will be a bis-allyl-functionalized flame-retardant phenol vanillin-derived monomer 505-1. Likewise, if process 500-1 is carried out with a phosphorus-based flame-retardant molecule 340 having an epoxide R group 408, the bis-functionalized flame-retardant phenol vanillin-derived monomer 505 will be a bis-epoxide-substituted flame-retardant phenol vanillin-derived monomer 505-2. If the process is carried out with the phosphate-based flame-retardant molecule 340-1, the bis-functionalized flame-retardant phenol vanillin-derived monomer 505 will have a phosphoryl FR group, and, if the reaction is carried out with the phosphonate-based flame-retardant molecule 340-2, the bis-functionalized flame-retardant phenol vanillin-derived monomer 505 will have a phosphonyl FR group.

Figure 5B:
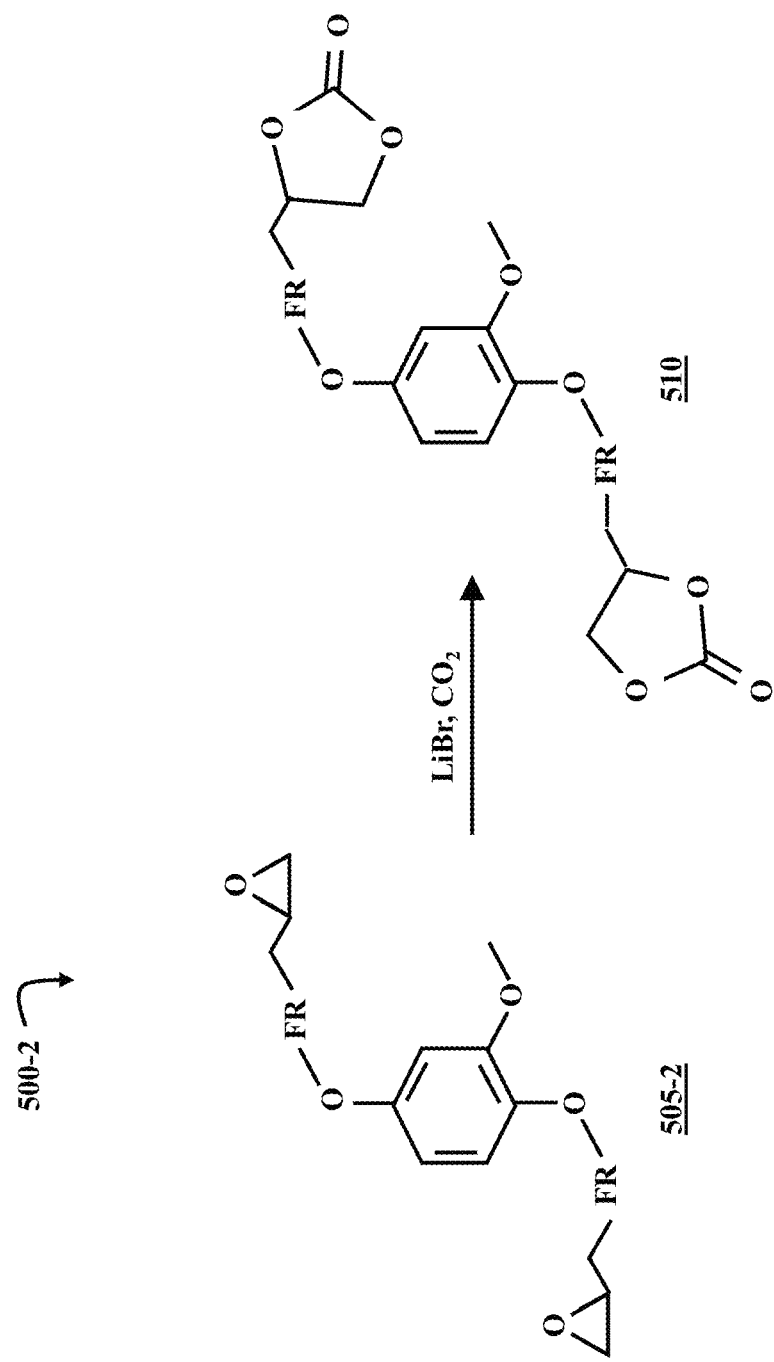
FIG. 5B is a chemical reaction diagram illustrating a process of synthesizing a bis-propylene-carbonate-functionalized flame-retardant phenol vanillin-derived monomer, according to some embodiments of the present disclosure.

FIG. 5B is a chemical reaction diagram illustrating a process 500-2 of synthesizing a bis-propylene-carbonate-functionalized flame-retardant phenol vanillin-derived monomer 510, according to some embodiments of the present disclosure. The bis-epoxide-functionalized flame-retardant phenol vanillin-derived monomer 505-2 of vanillin is combined with lithium bromide (LiBr). Carbon dioxide (CO$_2$) is added to the mixture, either by injecting into the headspace of the reaction flask, or by bubbling through the solution. This step yields the bis-propylene-carbonate-functionalized flame-retardant phenol vanillin-derived monomer 510.

Figure 5C:
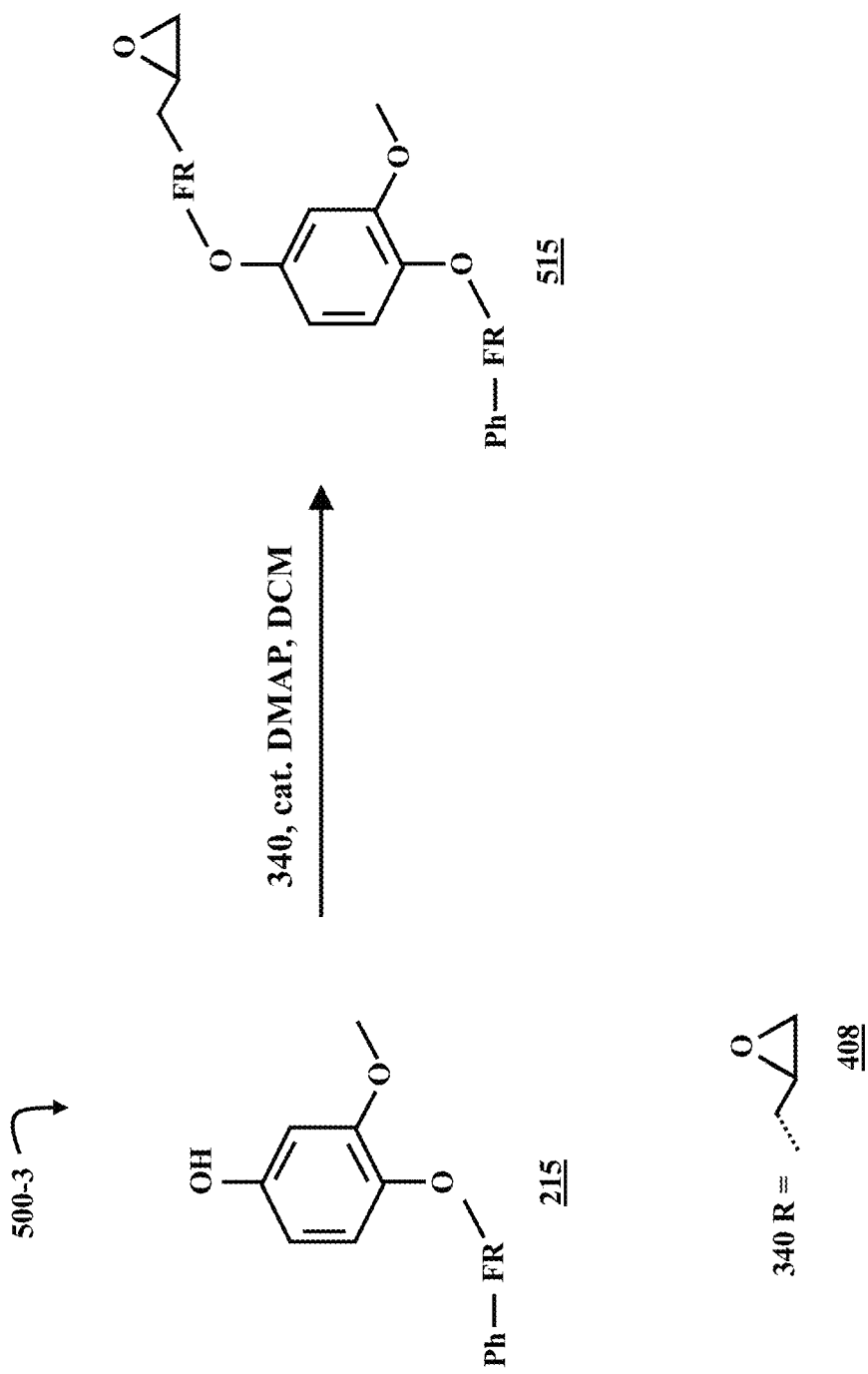
FIG. 5C is a chemical reaction diagram illustrating a process of synthesizing a mono-epoxide-functionalized flame-retardant phenol vanillin-derived monomer, according to some embodiments of the present disclosure.

FIG. 5C is a chemical reaction diagram illustrating a process 500-3 of synthesizing a mono-epoxide-functionalized flame-retardant phenol vanillin-derived monomer 515, according to some embodiments of the present disclosure. In process 500-3, the flame-retardant phenol derivative 215 is reacted with the phosphorus-based flame-retardant molecule 340 having an epoxide R group 408 and catalytic dimethylaminopyridine (DMAP) in a dichloromethane (DCM) solution. In some embodiments, stoichiometric triethylamine is used instead of DMAP. Stirring this mixture yields the mono-epoxide-functionalized flame-retardant phenol vanillin-derived monomer 515.

Figure 5D:
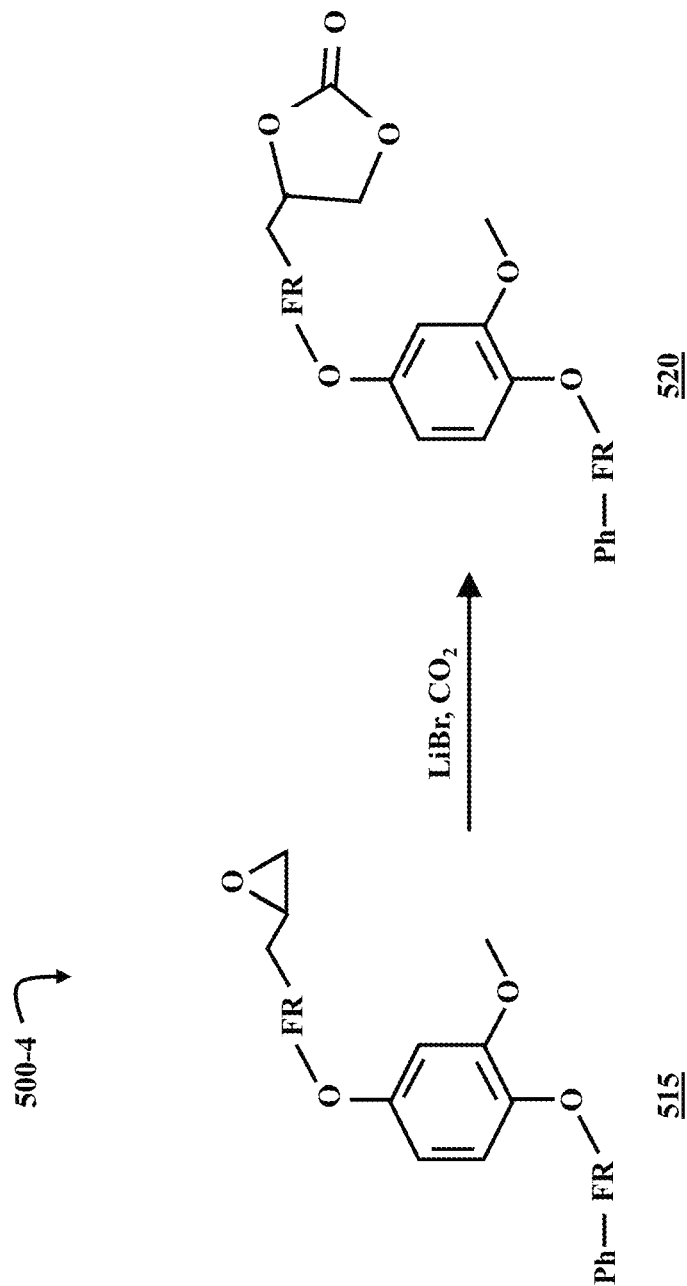
FIG. 5D is a chemical reaction diagram illustrating a process of synthesizing a mono-propylene-carbonate-functionalized flame-retardant phenol vanillin-derived monomer, according to some embodiments of the present disclosure.

FIG. 5D is a chemical reaction diagram illustrating a process 500-4 of synthesizing a mono-propylene-carbonate-functionalized flame-retardant phenol vanillin-derived monomer 520, according to some embodiments of the present disclosure. The mono-epoxide-functionalized flame-retardant phenol vanillin-derived monomer 515 is combined with lithium bromide (LiBr). Carbon dioxide (CO$_2$) is added to the mixture, either by injecting into the headspace of the reaction flask, or by bubbling through the solution. This step yields the mono-propylene-carbonate-functionalized flame-retardant phenol vanillin-derived monomer 520.

Figure 5E:
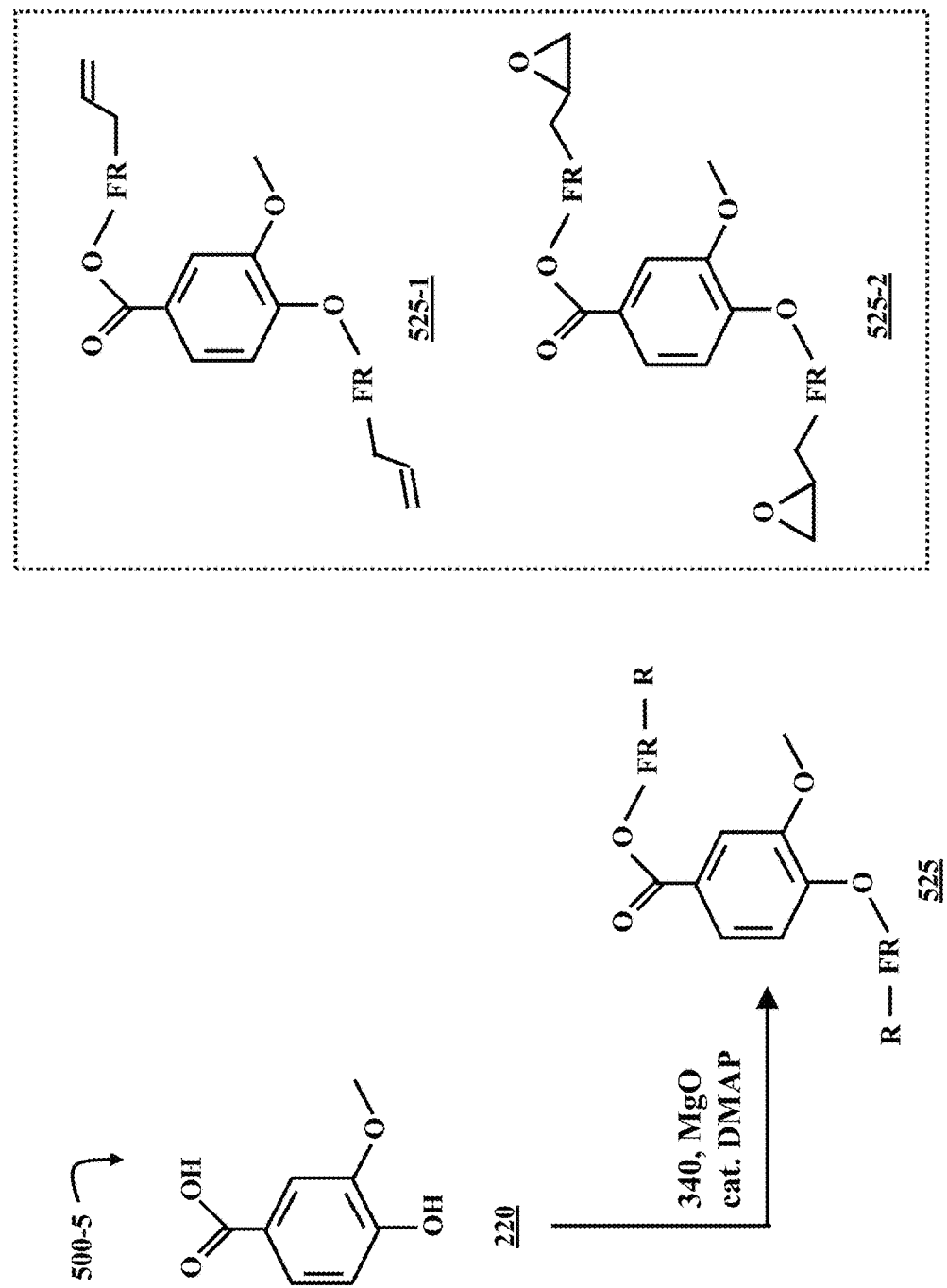
FIG. 5E is a chemical reaction diagram illustrating a process of synthesizing a bis-functionalized flame-retardant carboxylic acid vanillin-derived monomer, according to some embodiments of the present disclosure.

FIG. 5E is a chemical reaction diagram illustrating a process 500-5 of synthesizing a bis-functionalized flame-retardant carboxylic acid vanillin-derived monomer 525, according to some embodiments of the present disclosure. In process 500-5, the carboxylic acid diol vanillin-derived monomer 220 is reacted with a phosphorus-based flame-retardant molecule 340 and catalytic dimethylaminopyridine (DMAP) in a dichloromethane (DCM) solution. In some embodiments, stoichiometric triethylamine is used instead of DMAP. Stirring this mixture yields the bis-functionalized flame-retardant carboxylic acid vanillin-derived monomer 525.

If process 500-5 is carried out with a phosphorus-based flame-retardant molecule 340 having an allyl R group 407, the bis-functionalized flame-retardant carboxylic acid vanillin-derived monomer 525 will be a bis-allyl-functionalized flame-retardant carboxylic acid vanillin-derived monomer 525-1. Likewise, if process 500-5 is carried out with a phosphorus-based flame-retardant molecule 340 having an epoxide R group 408, the functionalized flame-retardant carboxylic acid vanillin-derived monomer 525 will be a bis-epoxide-functionalized flame-retardant carboxylic acid vanillin-derived monomer 525-2. If the process is carried out with the phosphate-based flame-retardant molecule 340-1, the bis-functionalized flame-retardant carboxylic acid vanillin-derived monomer 525 will have a phosphoryl FR group, and, if the reaction is carried out with the phosphonate-based flame-retardant molecule 340-2, the functionalized flame-retardant carboxylic acid vanillin-derived monomer 525 will have a phosphonyl FR group.

Figure 5F:
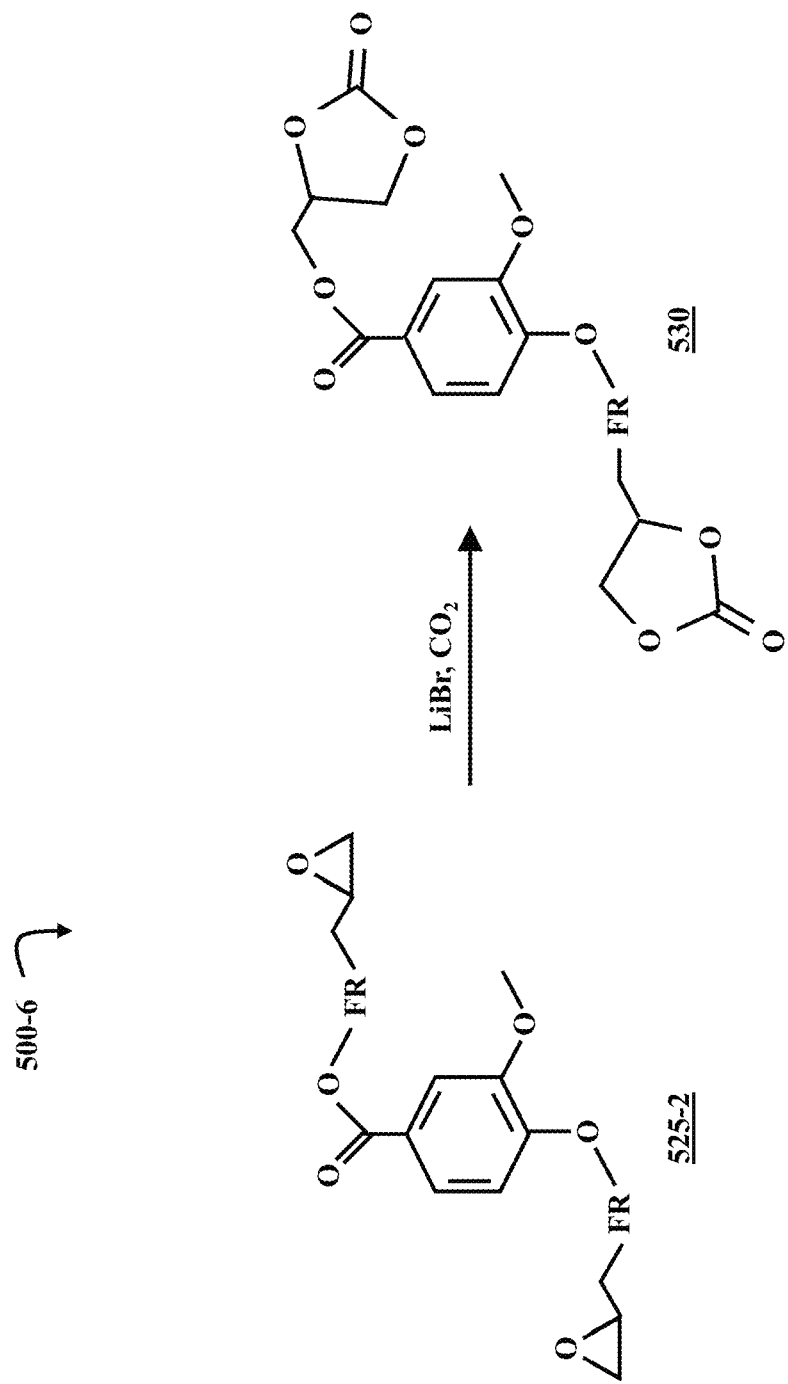
FIG. 5F is a chemical reaction diagram illustrating a process 500-6 of synthesizing a bis-propylene-carbonate-functionalized flame-retardant carboxylic acid vanillin-derived monomer 530, according to some embodiments of the present disclosure.

FIG. 5F is a chemical reaction diagram illustrating a process 500-6 of synthesizing a bis-propylene-carbonate-functionalized flame-retardant carboxylic acid vanillin-derived monomer 530, according to some embodiments of the present disclosure. The bis-epoxide-functionalized flame-retardant carboxylic acid vanillin-derived monomer 525-2 is combined with lithium bromide (LiBr). Carbon dioxide ($CO_2$) is added to the mixture, either by injecting into the headspace of the reaction flask, or by bubbling through the solution. This step yields the bis-propylene-carbonate-functionalized flame-retardant carboxylic acid vanillin-derived monomer 530.

Figure 5G:
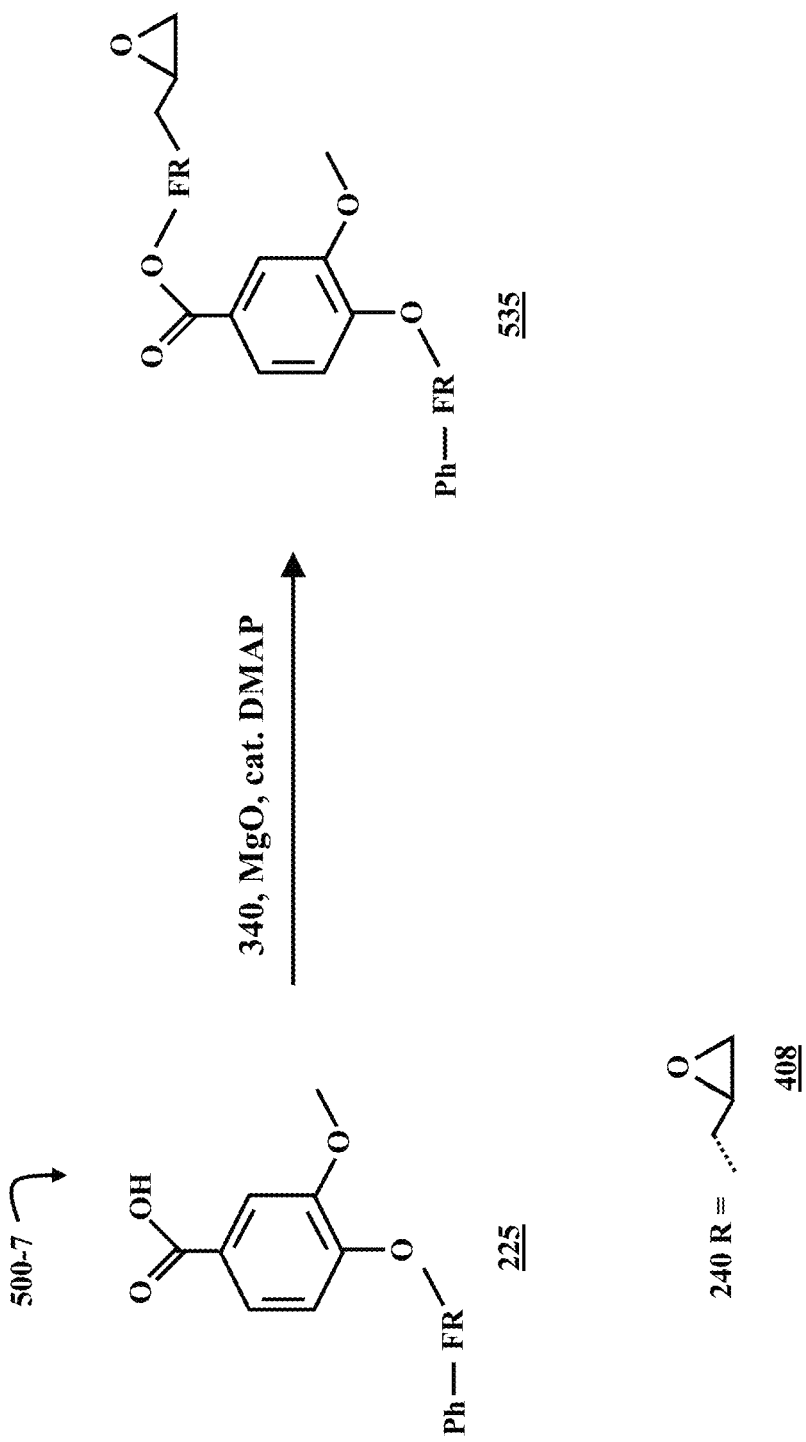
FIG. 5G is a chemical reaction diagram illustrating a process of synthesizing a mono-epoxide-functionalized flame-retardant carboxylic acid vanillin-derived monomer, according to some embodiments of the present disclosure.

FIG. 5G is a chemical reaction diagram illustrating a process 500-7 of synthesizing a mono-epoxide-functionalized flame-retardant carboxylic acid vanillin-derived monomer 535, according to some embodiments of the present disclosure. In process 500-7, the flame-retardant carboxylic acid vanillin-derived monomer 225 is reacted with the phosphorus-based flame-retardant molecule 340 having an epoxide R group 408 and catalytic dimethylaminopyridine (DMAP) in a dichloromethane (DCM) solution. In some embodiments, stoichiometric triethylamine is used instead of DMAP. Stirring this mixture yields the mono-epoxide-functionalized flame-retardant carboxylic acid vanillin-derived monomer 535.

Figure 5H:
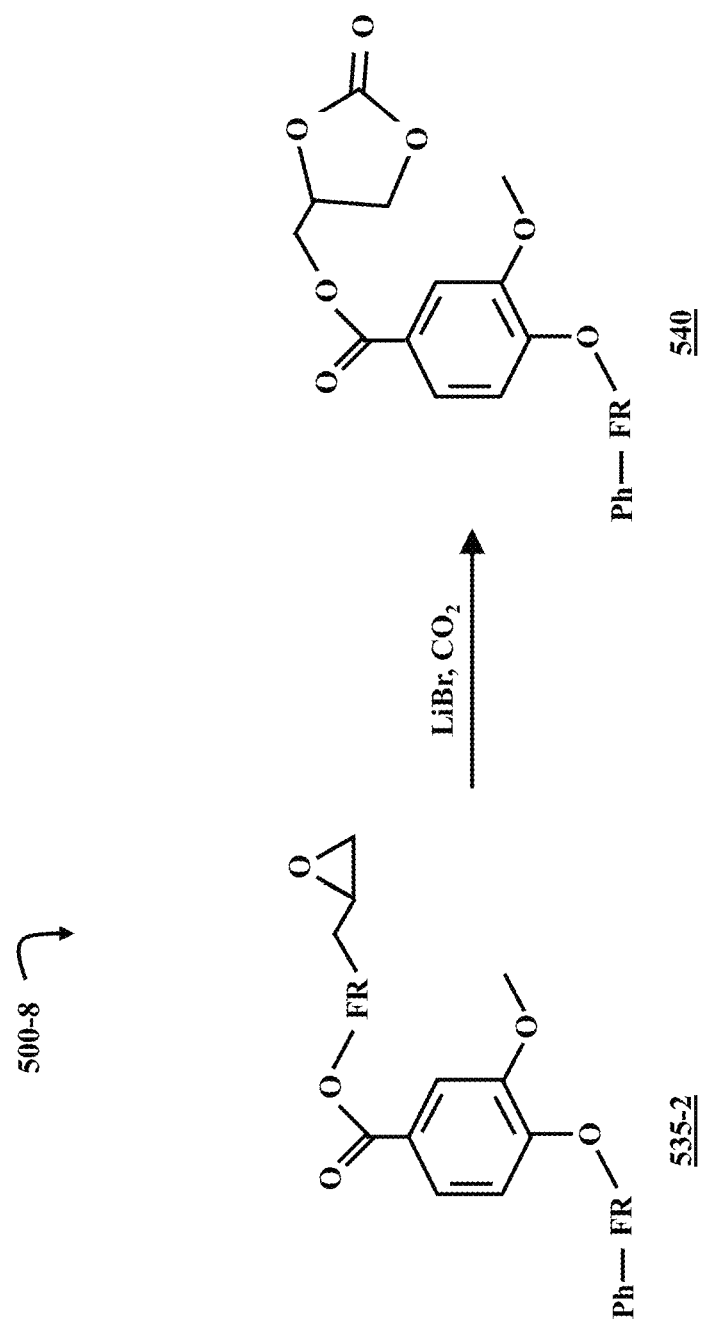
FIG. 5H is a chemical reaction diagram illustrating a process of synthesizing a mono-propylene-carbonate-functionalized flame-retardant carboxylic acid vanillin-derived monomer, according to some embodiments of the present disclosure.

FIG. 5H is a chemical reaction diagram illustrating a process 500-8 of synthesizing a mono-propylene-carbonate-functionalized flame-retardant carboxylic acid vanillin-derived monomer 540, according to some embodiments of the present disclosure. The mono-epoxide-functionalized flame-retardant carboxylic acid vanillin-derived monomer 535-2 is combined with lithium bromide (LiBr). Carbon dioxide ($CO_2$) is added to the mixture, either by injecting into the headspace of the reaction flask, or by bubbling through the solution. This step yields the mono-propylene-carbonate-functionalized flame-retardant carboxylic acid vanillin-derived monomer 540.

Figure 5I:
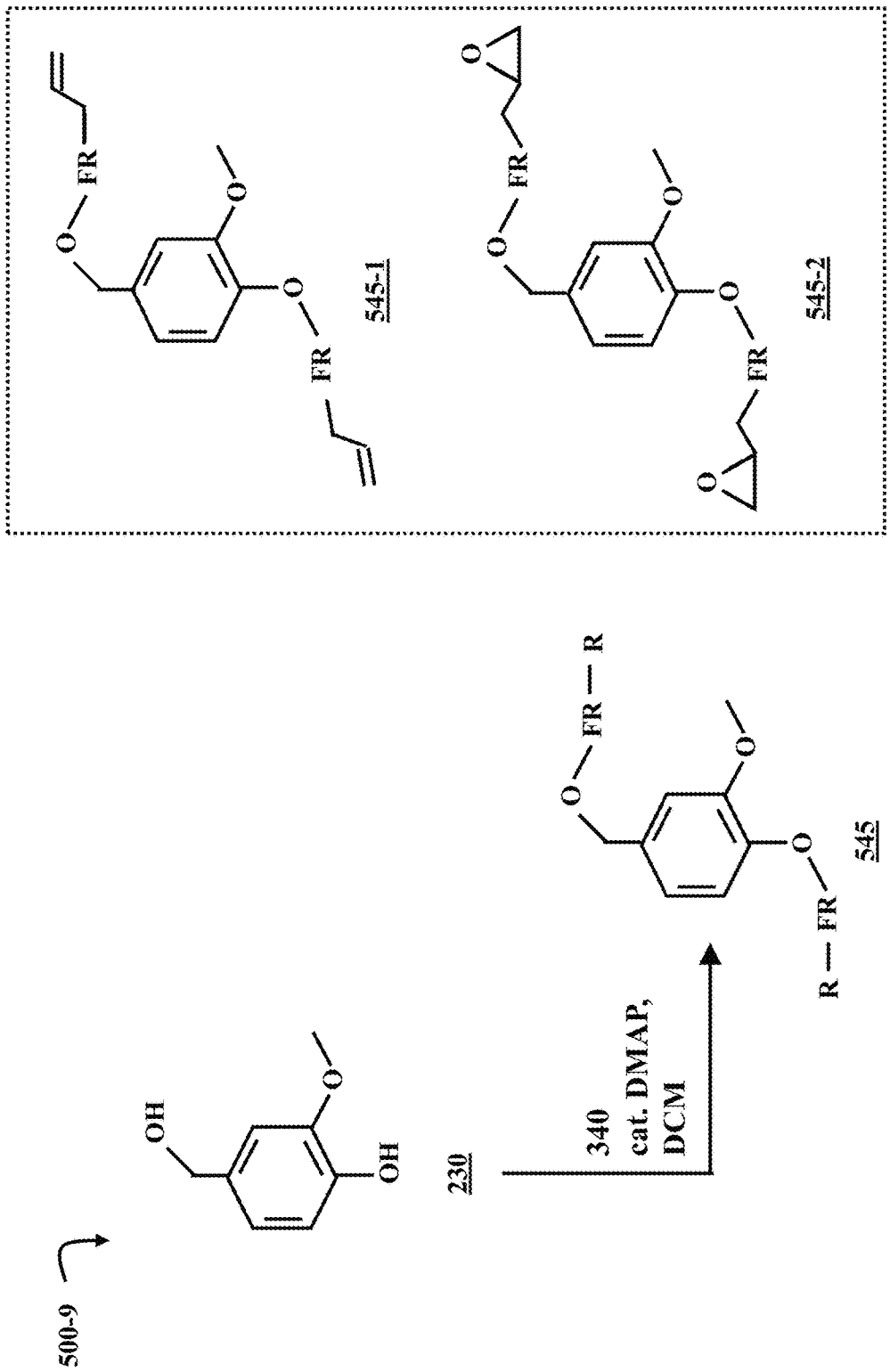
FIG. 5I is a chemical reaction diagram illustrating a process of synthesizing a bis-functionalized flame-retardant benzyl alcohol vanillin-derived monomer, according to some embodiments of the present disclosure.

FIG. 5I is a chemical reaction diagram illustrating a process 500-9 of synthesizing a bis-functionalized flame-retardant benzyl alcohol vanillin-derived monomer 545, according to some embodiments of the present disclosure. The benzyl alcohol diol derivative 230 of vanillin is reacted with a phosphorus-based flame-retardant molecule 340 and catalytic dimethylaminopyridine (DMAP) in a dichloromethane (DCM) solution. In some embodiments, stoichiometric triethylamine is used instead of DMAP. Stirring this mixture yields the bis-functionalized flame-retardant benzyl alcohol vanillin-derived monomer 545.

If process 500-9 is carried out with a phosphorus-based flame-retardant molecule 340 having an allyl R group 407, the bis-functionalized flame-retardant benzyl alcohol vanillin-derived monomer 545 will be a bis-allyl-functionalized flame-retardant benzyl alcohol vanillin-derived monomer 545-1. Likewise, if process 500-9 is carried out with a phosphorus-based flame-retardant molecule 340 having an epoxide R group 408, the bis-functionalized flame-retardant benzyl alcohol vanillin-derived monomer 545 will be a bis-epoxide-substituted flame-retardant benzyl alcohol vanillin-derived monomer 545-2. If the reaction is carried out with the phosphate-based flame retardant molecule 340-1, the bis-functionalized flame retardant benzyl alcohol vanillin-derived monomer 545 will have phosphoryl FR groups, and, if the reaction is carried out with the phosphonate-based flame-retardant molecule 340-2, the bis-functionalized flame-retardant benzyl alcohol vanillin-derived monomer 545 will have phosphonyl FR groups.

Figure 5J:
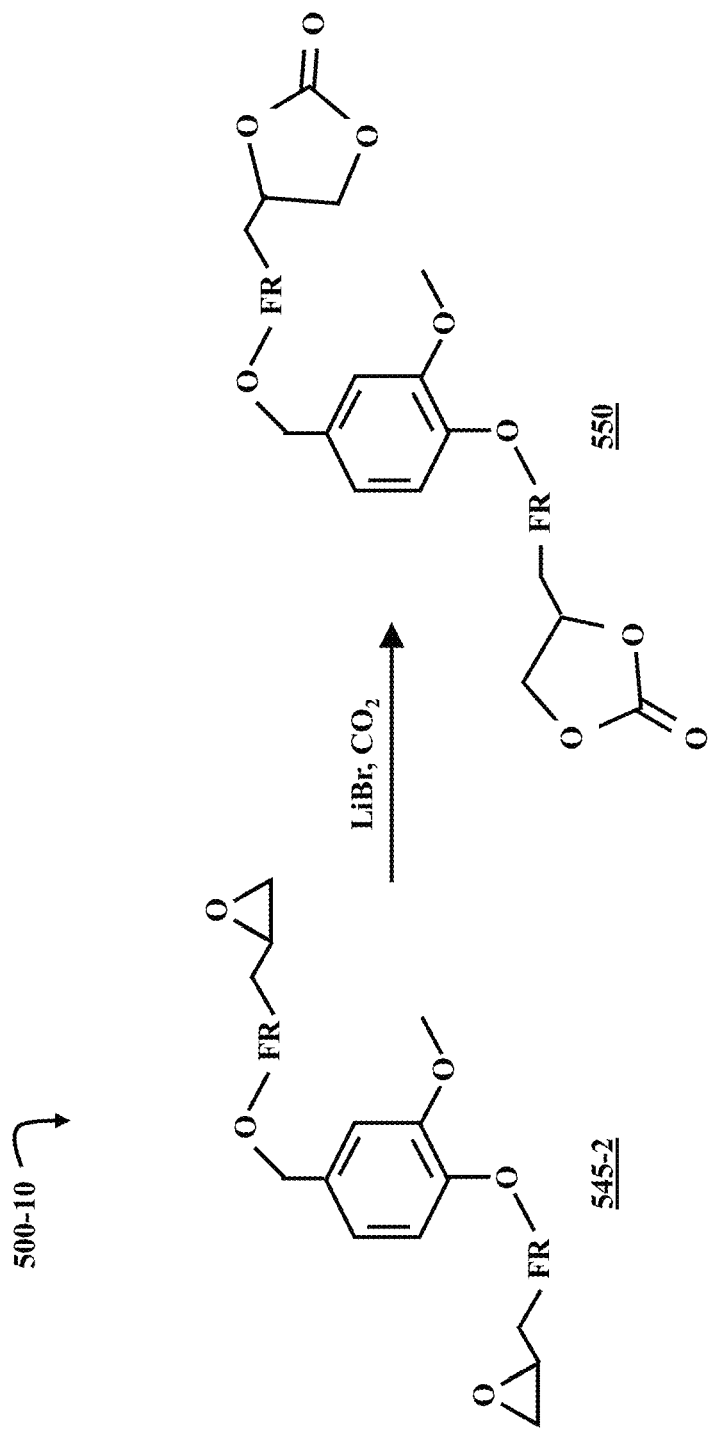
FIG. 5J is a chemical reaction diagram illustrating a process of synthesizing a bis-propylene-carbonate-functionalized flame-retardant benzyl alcohol vanillin-derived monomer, according to some embodiments of the present disclosure.

FIG. 5J is a chemical reaction diagram illustrating a process 500-10 of synthesizing a bis-propylene-carbonate-functionalized flame-retardant benzyl alcohol vanillin-derived monomer 550, according to some embodiments of the present disclosure. The bis-epoxide-functionalized flame-retardant benzyl alcohol vanillin-derived monomer 545-2 is combined with lithium bromide (LiBr). Carbon dioxide ($CO_2$) is added to the mixture, either by injecting into the headspace of the reaction flask, or by bubbling through the solution. The reaction yields the bis-propylene-carbonate-functionalized flame-retardant benzyl alcohol vanillin-derived monomer 550.

Figure 5K:
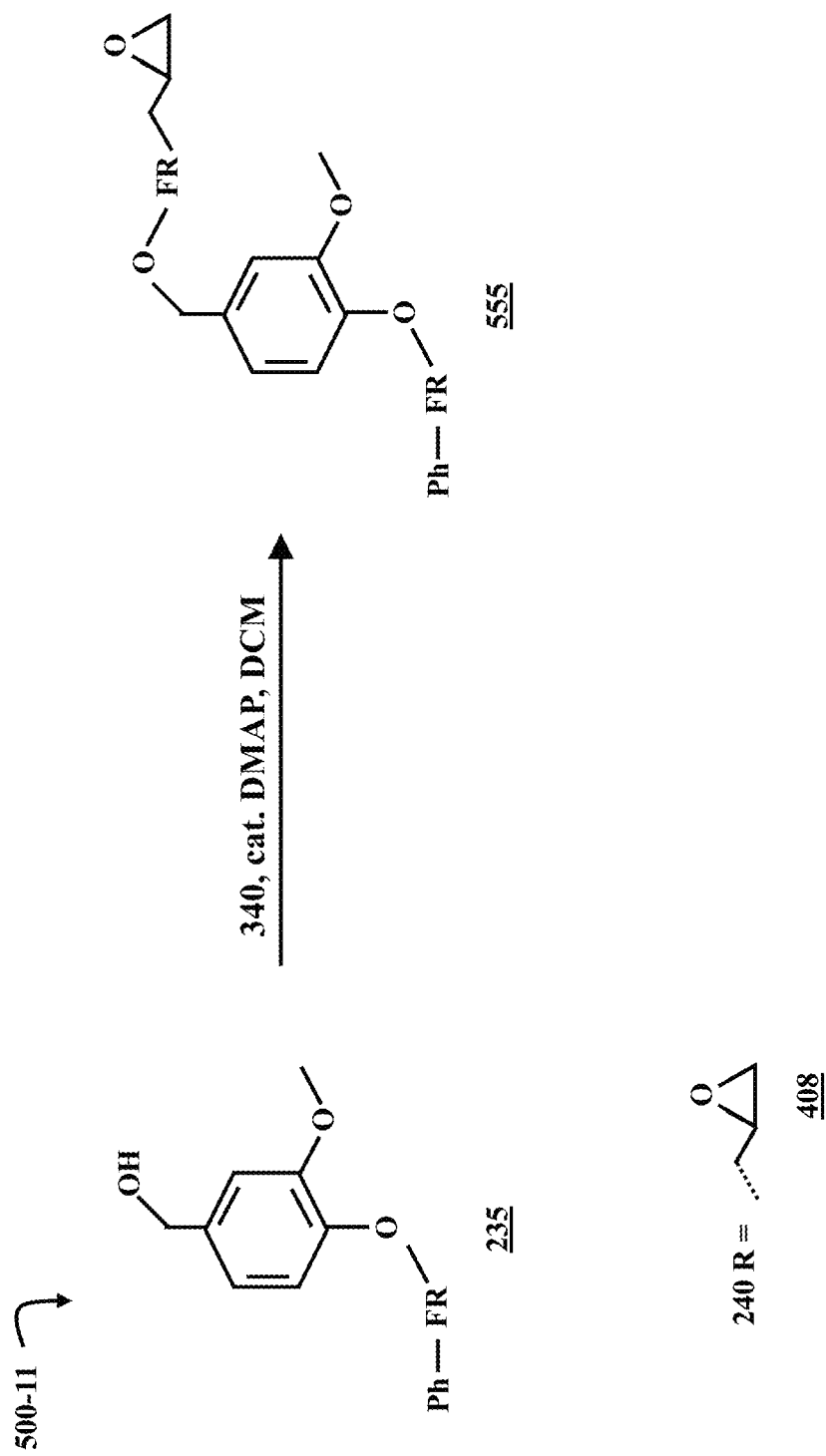
FIG. 5K is a chemical reaction diagram illustrating a process of synthesizing a mono-epoxide-functionalized flame-retardant benzyl alcohol vanillin-derived monomer, according to some embodiments of the present disclosure.

FIG. 5K is a chemical reaction diagram illustrating a process 500-11 of synthesizing a mono-epoxide-functionalized flame-retardant benzyl alcohol vanillin-derived monomer 555, according to some embodiments of the present disclosure. In process 500-11, the flame-retardant benzyl alcohol derivative 235 is reacted with the phosphorus-based flame-retardant molecule 340 having an epoxide R group 408 and catalytic dimethylaminopyridine (DMAP) in a dichloromethane (DCM) solution. In some embodiments, stoichiometric triethylamine is used instead of DMAP. Stirring this mixture yields the mono-epoxide-functionalized flame-retardant benzyl alcohol vanillin-derived monomer 555.

Figure 5L:
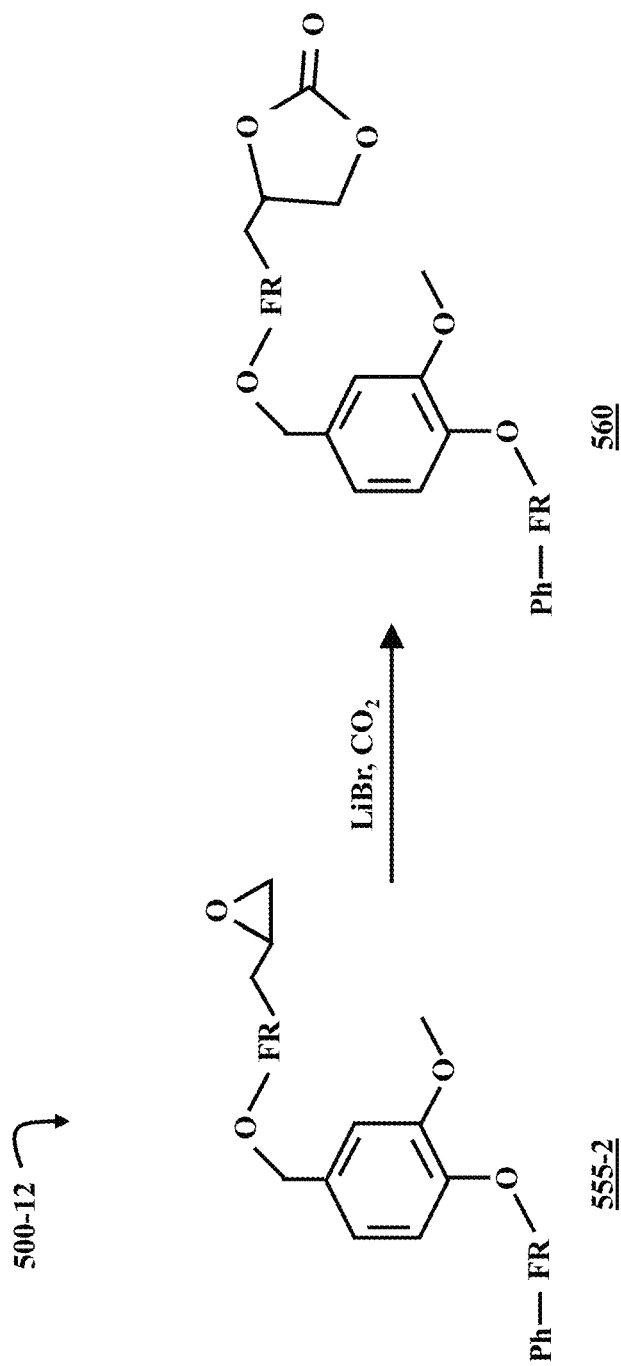
FIG. 5L is a chemical reaction diagram illustrating a process of synthesizing a mono-propylene-carbonate-functionalized flame-retardant benzyl alcohol vanillin-derived monomer, according to some embodiments of the present disclosure.

FIG. 5L is a chemical reaction diagram illustrating a process 500-12 of synthesizing a mono-propylene-carbonate-functionalized flame-retardant benzyl alcohol vanillin-derived monomer 560, according to some embodiments of the present disclosure. The mono-epoxide-functionalized flame-retardant benzyl alcohol vanillin-derived monomer 555-2 is combined with lithium bromide (LiBr). Carbon dioxide ($CO_2$) is added to the mixture, either by injecting into the headspace of the reaction flask, or by bubbling through the solution. This step yields the mono-propylene-carbonate-functionalized flame-retardant benzyl alcohol vanillin-derived monomer 560.

In some embodiments, the processes of forming substituted flame-retardant vanillin-derived monomers illustrated in FIGS. 5A, 5C, 5E, 5G, 5I and 5K are carried out with a mixture of both the phosphate-based 340-1 and the phosphonate-based 340-2 flame retardant molecules. Carrying out these reactions with a mixture of the phosphate-340-1 and phosphonate-based 340-2 flame retardant molecules can result in substituted flame-retardant vanillin-derived monomers with both phosphoryl and phosphonyl FR groups.

However, in some instances, adding a mixture of phosphate-340-1 and phosphonate-based 340-2 flame retardant molecules can result in the production of functionalized flame-retardant vanillin-derived monomers with all phosphoryl or all phosphonyl FR groups. Additionally, adding both phosphate-340-1 and phosphonate-based 340-2 flame retardant molecules to the reaction can yield a mixture of products that includes some combination of derivatives with either all phosphoryl or all phosphonyl FR groups and derivatives with both phosphoryl and phosphonyl FR groups.

Figure 6A:
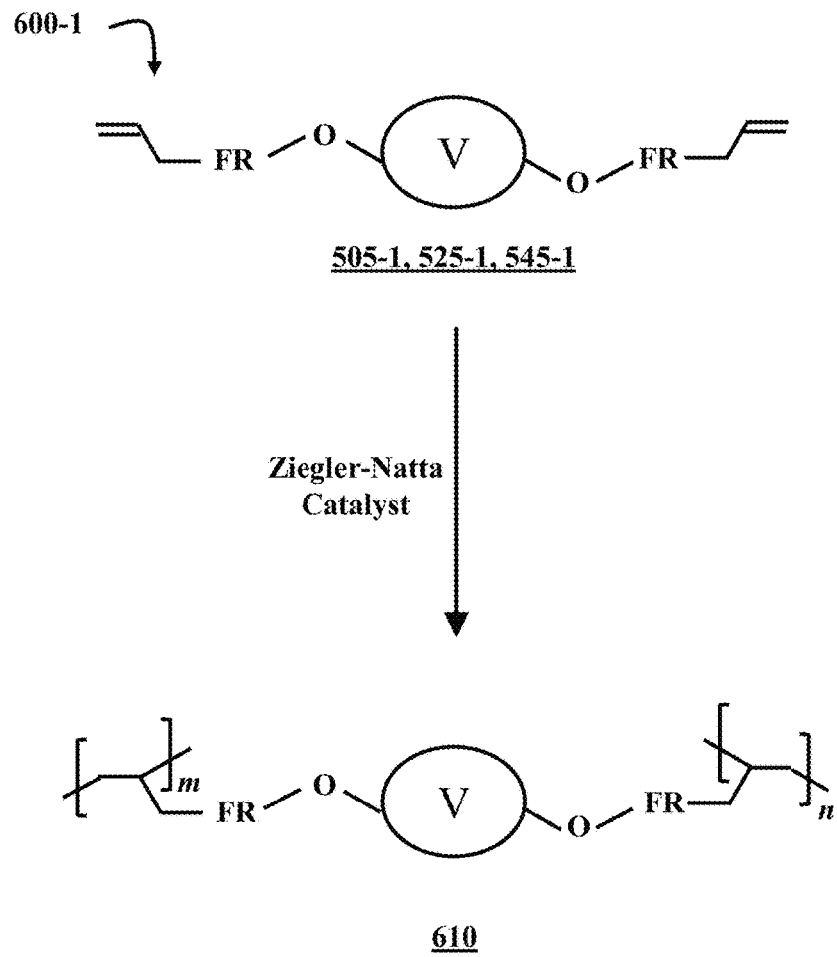
FIG. 6A is a chemical reaction diagram illustrating a process of forming flame-retardant vanillin-based polymers derived from the bis-allyl-functionalized vanillin-derived monomers, according to some embodiments of the present disclosure.
Figure 6A:
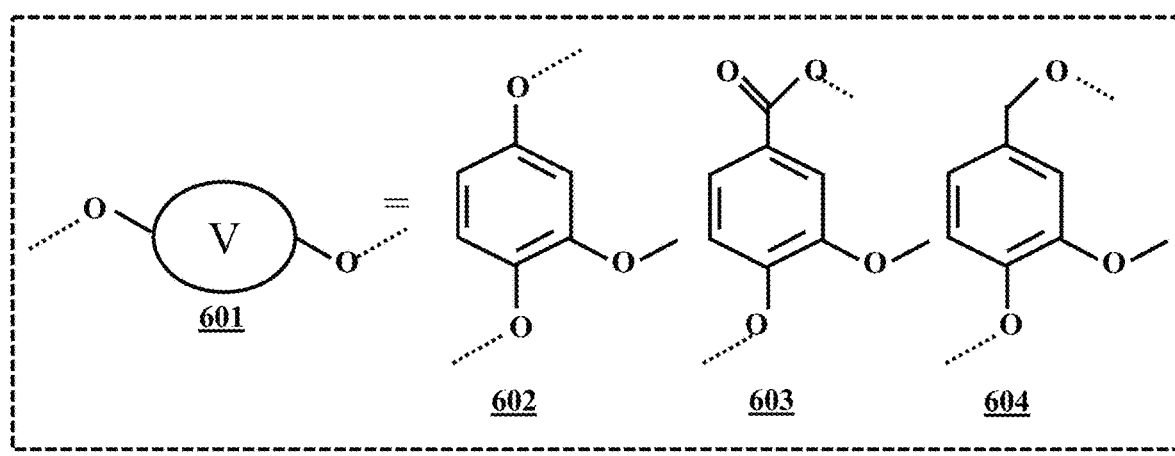

FIG. 6A is a chemical reaction diagram illustrating a process 600-1 of forming flame-retardant vanillin-based polymers 610 derived from the bis-allyl-functionalized vanillin-derived monomers 505-1, 525-1, and 545-1, according to some embodiments of the present disclosure. The allyl-functionalized vanillin derivative polymer 610 is shown having an oval 601 representing the vanillin moiety in the flame-retardant vanillin-derived monomer 108 in order to simplify the illustration of the molecule structure. The oval can be a phenol-derived moiety 602 from either the phenol diol vanillin derivative 210 or the phenol flame-retardant vanillin derivative 215, a carboxylic acid-derived moiety 603 from either the carboxylic acid diol vanillin derivative 220 or the carboxylic acid flame-retardant vanillin derivative 225, or a benzyl alcohol-derived moiety 604 from either the benzyl alcohol diol vanillin derivative 230 or the benzyl alcohol flame-retardant vanillin derivative 235.

In process 600-1, the flame-retardant vanillin-based polymers 610 derived from the bis-allyl-functionalized vanillin-derived monomers are formed by reacting a bis-allyl-functionalized vanillin-derived monomer 505-1, 525-1, or 545-1 with a Ziegler-Natta catalyst. Ziegler-Natta catalysts catalyze the polymerization of 1-alkenes. Examples of these catalysts can include heterogeneous Ziegler-Natta catalysts based titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

Figure 6B:
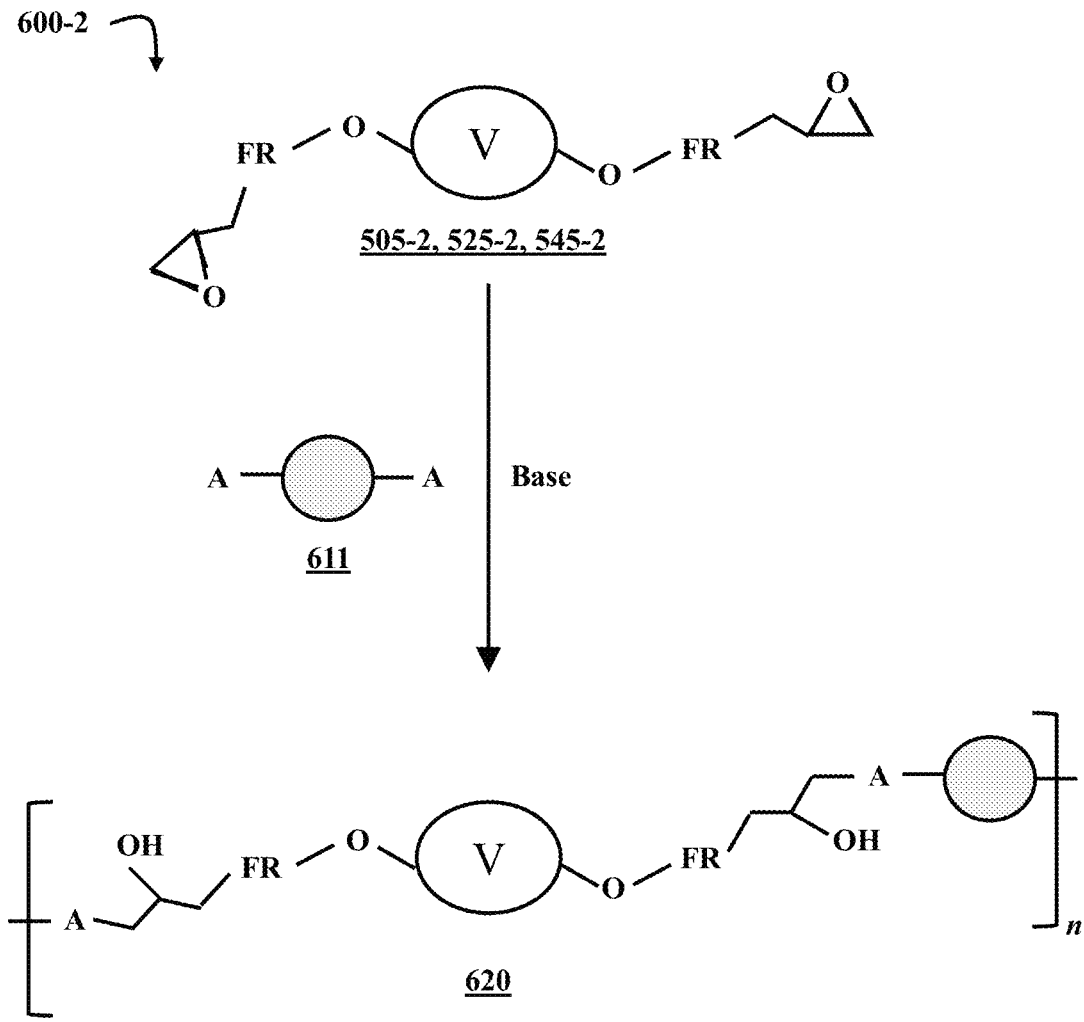
FIG. 6B is a chemical reaction diagram illustrating a process of forming flame-retardant vanillin-based polymers derived from the bis-epoxide-functionalized vanillin-derived monomers, according to some embodiments of the present disclosure.

FIG. 6B is a chemical reaction diagram illustrating a process 600-2 of forming flame-retardant vanillin-based polymers 620 derived from the bis-epoxide-functionalized vanillin-derived monomers, 505-2, 525-2, and 545-2, according to some embodiments of the present disclosure. The bis-epoxide-functionalized vanillin-derived monomer 505-2, 525-2, or 545-2 is reacted with a base and a compound with at least two hydroxyl (OH) groups or at least two amino ($NH_2$) groups (e.g., a diol, polyol, diamine, polyamine, etc.) 611. These compounds 611 are illustrated as a gray oval with attached A groups. The A group represents a hydroxyl group or an amino group. It should be noted that, while two A groups are illustrated, there can be more than two A groups in some embodiments. Additionally, in some embodiments, the bis-epoxide functionalized vanillin-derived monomer 505-2, 525-2, or 545-2 self-polymerizes under basic conditions. In these instances, the reaction does not include the compound with at least two hydroxyl groups or at least two amino groups 611.

Figure 6C:
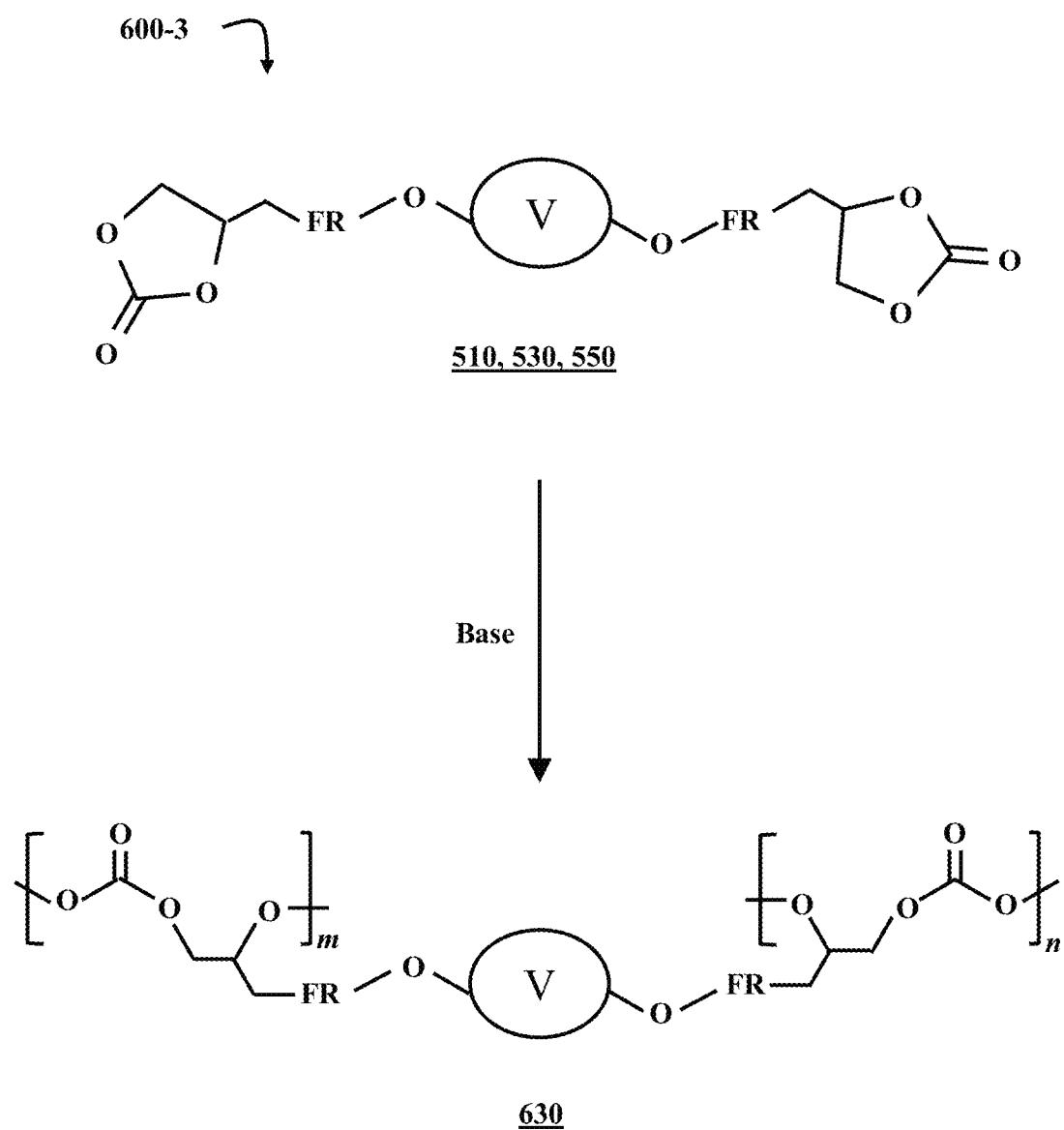
FIG. 6C is a chemical reaction diagram illustrating a process of forming flame-retardant vanillin-based polymers derived from the bis-propylene-carbonate-functionalized vanillin-derived monomers, according to some embodiments of the present disclosure.

FIG. 6C is a chemical reaction diagram illustrating a process 600-3 of forming flame-retardant vanillin-based polymers 630 derived from the bis-propylene-carbonate-functionalized vanillin-derived monomers 510, 530, and 550, according to some embodiments of the present disclosure. In process 600-3, a bis-propylene-carbonate-functionalized vanillin-derived monomer 510, 530, or 550 is reacted in a ring-opening polymerization initiated by a base. Examples of bases that can be used as initiators can include potassium hydroxide, sodium hydroxide, lithium hydroxide, etc.

Figure 6D:
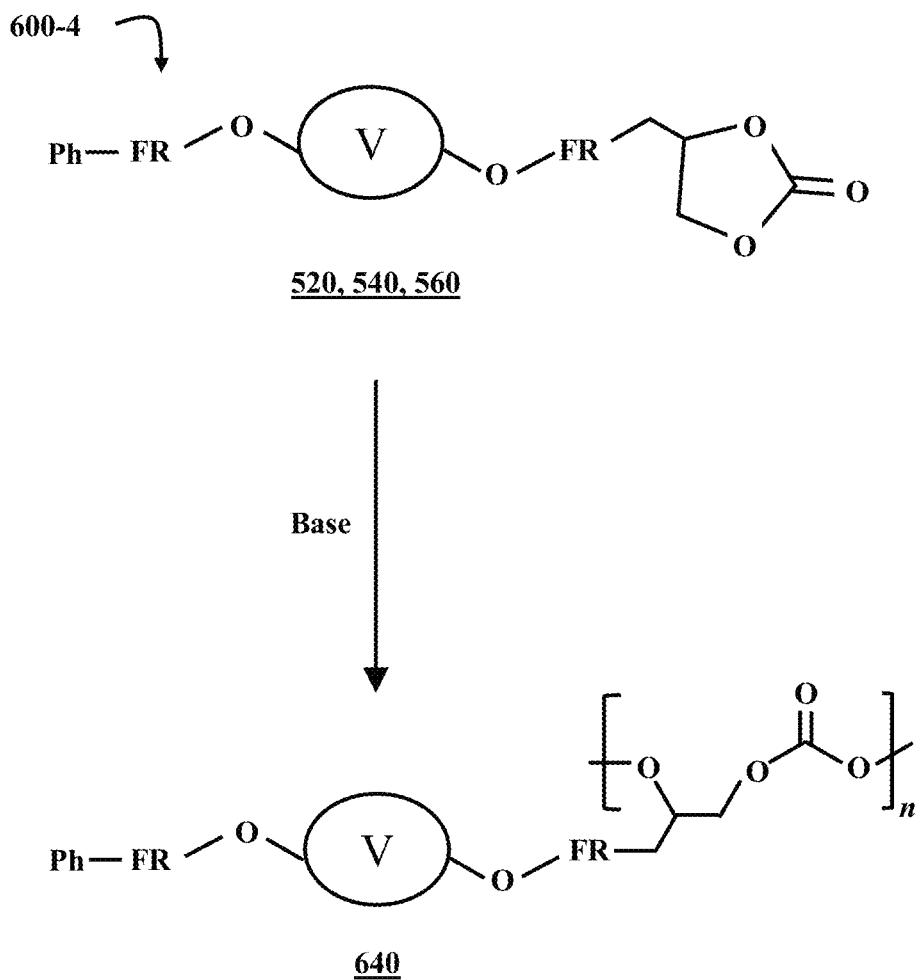
FIG. 6D is a chemical reaction diagram illustrating a process of forming flame-retardant vanillin-based polymers derived from the mono-propylene-carbonate-functionalized vanillin-derived monomers, according to some embodiments of the present disclosure.

FIG. 6D is a chemical reaction diagram illustrating a process 600-4 of forming flame-retardant vanillin-based polymers 640 derived from the mono-propylene-carbonate-functionalized vanillin-derived monomers 520, 540, and 560, according to some embodiments of the present disclosure. In process 600-4, the mono-propylene-carbonate-functionalized vanillin-derived monomer 520, 540, or 560 is reacted in a ring-opening polymerization initiated by a base. Examples of bases that can be used as initiators can include potassium hydroxide, sodium hydroxide, lithium hydroxide, etc.

In addition to the polymers 610, 620, 630, and 640 illustrated in FIGS. 6A-6D, the flame-retardant vanillin-derived monomers 108 disclosed herein can be used in the synthesis of other flame-retardant polymers. An array of classes of flame-retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, polycarbonates, epoxy resins, polyimides, polyureas, polyamides, poly(vinyl-esters), etc.

One example of an application of polymers made, at least in part, from flame-retardant vanillin-derived monomers 108 is in plastics used in electronics hardware. Additional applications can include acoustic dampening, cushioning, plastics, synthetic fibers, insulation, adhesives, etc. The flame-retardant vanillin-derived monomers 108 can also be used to make adhesives such as bio-adhesives, elastomers, thermoplastics, emulsions, thermosets, etc. Further, materials containing the flame-retardant vanillin-derived monomers 108 can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating polymers that are made, at least in part, from flame-retardant vanillin-derived monomers 108. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polyurethane, a polycarbonate, a polyester, a polyacrylate, a polyimide, a polyamide, a polyurea, a poly(vinyl-ester), etc. Using polymers that incorporate the flame-retardant vanillin-derived monomers 108 can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. In some instances, reactions that involve multiple steps can be carried out sequentially, and, in other instances, they can be carried out in one pot. Further, in some embodiments, processes can be added or omitted while still remaining within the scope of the disclosure, as will be understood by a person of ordinary skill in the art.

What is claimed is:

1. A process of forming a flame-retardant polymer, comprising:
    forming a phosphorus-based flame-retardant molecule selected from the group consisting of a chlorophosphate-based molecule and a phosphonate-based molecule;
    forming a vanillin derivative;
    chemically reacting the vanillin derivative with the phosphorus-based flame-retardant molecule to form a flame-retardant vanillin-derived monomer; and
    polymerizing the flame-retardant vanillin-derived monomer.

2. The process of claim 1, wherein the vanillin derivative is synthesized from vanillin that has been obtained from a bio-based source.

3. The process of claim 1, wherein the vanillin derivative is a diol vanillin derivative selected from a group consisting of:
    a phenol diol vanillin derivative with a formula of:

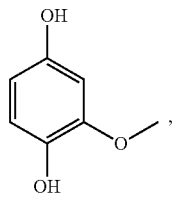

a carboxylic acid diol vanillin derivative with a formula of:

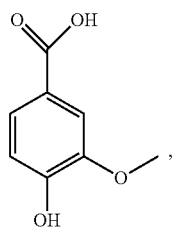

and
a benzyl alcohol diol vanillin derivative with a formula of:

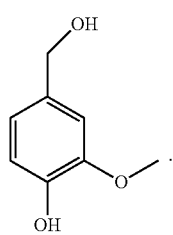

4. The process of claim 1, wherein the vanillin derivative is a flame-retardant vanillin derivative selected from a group consisting of:
    a flame-retardant phenol vanillin derivative with a formula of:

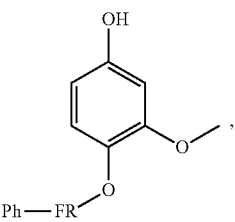

wherein FR is a phosphorus-based moiety and Ph is a phenyl substituent,
    a flame-retardant carboxylic acid vanillin derivative with a formula of:

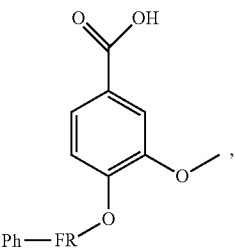

wherein FR is a phosphorus-based moiety and Ph is a phenyl substituent, and
    a flame-retardant benzyl alcohol vanillin derivative with a formula of:

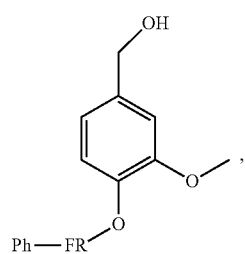

wherein FR is a phosphorus-based moiety and Ph is a phenyl substituent.

5. The process of claim 4, wherein the FR is a phosphoryl moiety with a formula of:

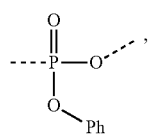

wherein Ph is a phenyl substituent.

6. The process of claim 4, wherein the FR is a phosphonyl moiety with a formula of:

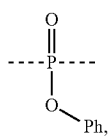

wherein Ph is a phenyl substituent.

7. The process of claim 1, wherein the phosphorus-based flame-retardant molecule has a formula of:

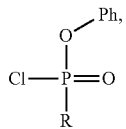

wherein Ph is a phenyl substituent and R is a substituent selected from a group consisting of an epoxide substituent and an allyl substituent.

8. The process of claim 1, wherein the phosphorus-based flame-retardant molecule has a formula of:

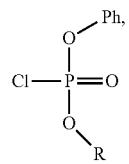

wherein Ph is a phenyl substituent and R is a substituent selected from the group consisting of the epoxide substituent and the allyl substituent.

9. The process of claim 1, further comprising chemically reacting the flame-retardant vanillin-derived monomer with lithium bromide and carbon dioxide to form a flame-retardant vanillin-derived monomer with at least one propylene carbonate substituent.

\* \* \* \* \*